(12) United States Patent
Erbs et al.

(10) Patent No.: US 9,180,150 B2
(45) Date of Patent: Nov. 10, 2015

(54) POXVIRAL ONCOLYTIC VECTORS

(75) Inventors: Philippe Erbs, Dagneux (FR); Johann Foloppe, Strasbourg (FR)

(73) Assignee: Transgene S.A., Illkirch (FR)

( * ) Notice: Subject to any disclaimer, the term of this patent is extended or adjusted under 35 U.S.C. 154(b) by 645 days.

(21) Appl. No.: 12/743,412

(22) PCT Filed: Nov. 17, 2008

(86) PCT No.: PCT/EP2008/009721
§ 371 (c)(1),
(2), (4) Date: Oct. 29, 2010

(87) PCT Pub. No.: WO2009/065547
PCT Pub. Date: May 28, 2009

(65) Prior Publication Data
US 2011/0044948 A1    Feb. 24, 2011

(30) Foreign Application Priority Data
Nov. 19, 2007    (EP) .................................... 07301556

(51) Int. Cl.
*A61K 35/768*    (2015.01)
*C07K 14/005*    (2006.01)
*C12N 15/86*    (2006.01)
*A61K 38/45*    (2006.01)
*A61K 38/50*    (2006.01)

(52) U.S. Cl.
CPC .............. *A61K 35/768* (2013.01); *A61K 38/45* (2013.01); *A61K 38/50* (2013.01); *C07K 14/005* (2013.01); *C12N 15/86* (2013.01); *C12N 2710/24122* (2013.01); *C12N 2710/24132* (2013.01); *C12N 2710/24143* (2013.01)

(58) Field of Classification Search
CPC ................... A61K 35/768; C12N 2710/24132
See application file for complete search history.

(56) References Cited

U.S. PATENT DOCUMENTS

| | | | |
|---|---|---|---|
| 5,364,773 A | 11/1994 | Paoletti et al. | |
| 8,105,578 B2 * | 1/2012 | Roberts et al. | 424/93.6 |
| 8,778,328 B2 * | 7/2014 | Erbs et al. | 424/93.2 |
| 2003/0031681 A1 * | 2/2003 | McCart et al. | 424/186.1 |
| 2003/0044384 A1 * | 3/2003 | Roberts et al. | 424/93.2 |
| 2005/0163758 A1 * | 7/2005 | Chiocca et al. | 424/93.2 |

FOREIGN PATENT DOCUMENTS

EP    1367128 A1    12/2003

OTHER PUBLICATIONS

Howley et al (Gene 172:233-237, 1996).*
Perkus et al (Virology 180:406-410, 1991).*
Thorne et al (Current Gene Therapy 5:429-443, 2005).*
A.W. Studebaker et al., *Novel Approaches for Modulating dUTPase and Uracil-DNA Glycosylase: Potential Uses for Cancer and Viral Chemotherapy*, 1(1) Drug Design Reviews 1-13 (2004).
Gnant et al., "Systemic Administration of a Recombinant Vaccinia Virus Expressing the Cytosine Deaminase Gene and Subsequent Treatment with 5-Fluorocytosine Leads to Tumor-specific Gene Expression and Prolongation of Survival in Mice," 59 Cancer Research 3396-3403 (Jul. 15, 1999).
Official Action dated Mar. 11, 2011, issued by the Canadian Patent Office in corresponding Canadian Patent Application No. 2,705,873.
Foloppe et al., "Targeted delivery of a suicide gene to human colorectal tumors by a conditionally replicating vaccinia virus", Gene Therapy, 2008, pp. 1361-1371, vol. 15, Macmillan Publishers Limited.
Roseman et al., "Purification and characterization of the Vaccinia virus deoxyuridine triphosphatase expressed in *Escherichia coli*", The Journal of Biological Chemistry, 1996, pp. 23506-23511, vol. 271, No. 38, The American Society for Biochemistry and Molecular Biology, Inc.
Zhang et al., "Eradication of solid human breast tumors in nude mice with an intravenously injected light-emitting oncolytic vaccinia virus", Cancer Res., 2007, pp. 10038-10046, vol. 67, No. 20, Baltimore, MD.
Erbs et al., "Modified vaccinia virus Ankara as a vector for suicide gene therapy", Cancer Gene Therapy, 2007, pp. 18-28, vol. 15, Nature Publishing Group.
Perkus et al., "Deletion of 55 open reading frames from the Termini of Vaccinia virus", Virology, 1991, pp. 406-410, vol. 180, Academic Press, Inc., Orlando, FL.
Prichard et al., "Vaccinia virus lacking the deoxyuridine triphosphatase gene (F2L) replicates well in vitro and in vivo, but is hypersensitive to the antiviral drug (N)-methanocarbathymidine", Virology Journal 2008, pp. 1-6, vol. 5, No. 39.
International Search Report corresponding to PCT/EP/2008/009721 mailed May 26, 2009.
S. Child et al., *Insertional Inactivation of the Large Subunit of Ribonucleotide Reductase Encoded by Vaccinia Virus Is Associated with Reduced Virulence In Vivo*, 174 Virology 625-629 (1990).
Russian Office Action mailed on Feb. 18, 2013, issued in corresponding Russian Patent Application No. 2010124613/10(035057) with English translation.
Notification of Reasons for Rejection with English translation mailed on Aug. 16, 2013, issued in corresponding Japanese Patent Application No. 2010-533511.
Goebel et al., *The Complete DNA Sequence of Vaccinia Virus*, 179 Virology 247-266 (1990).

* cited by examiner

*Primary Examiner* — Mary E Mosher
(74) *Attorney, Agent, or Firm* — Buchanan Ingersoll & Rooney PC

(57) ABSTRACT

A poxvirus comprising a defective F2L gene and compositions comprising such poxvirus are useful for therapeutic purposes, and more particularly for the treatment of cancer.

6 Claims, 10 Drawing Sheets

Figure 1:
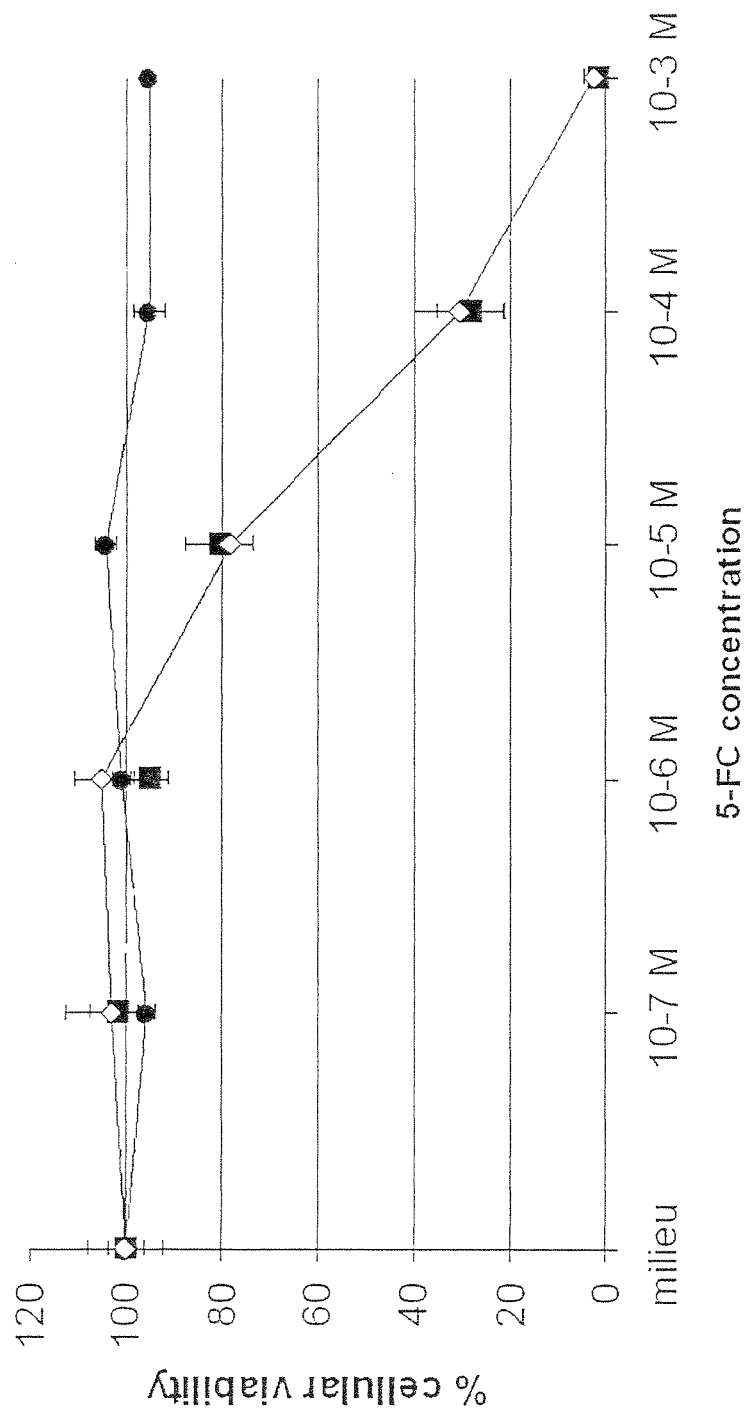

Figure 4
(A)
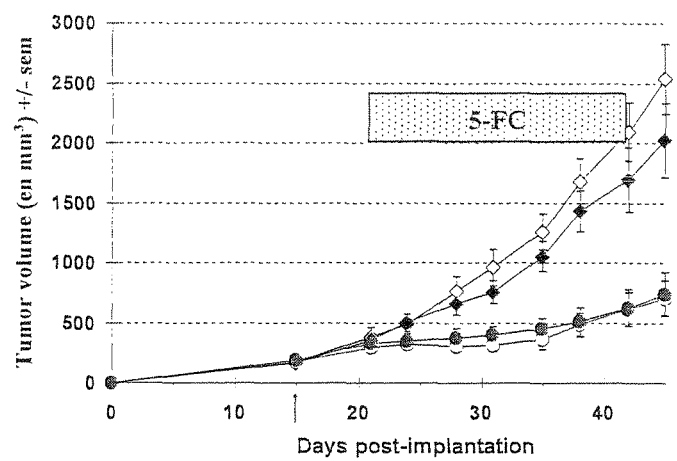
(B)
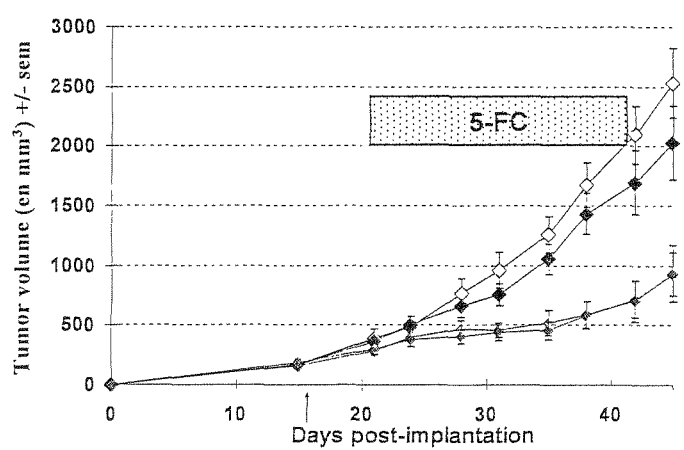

(A)
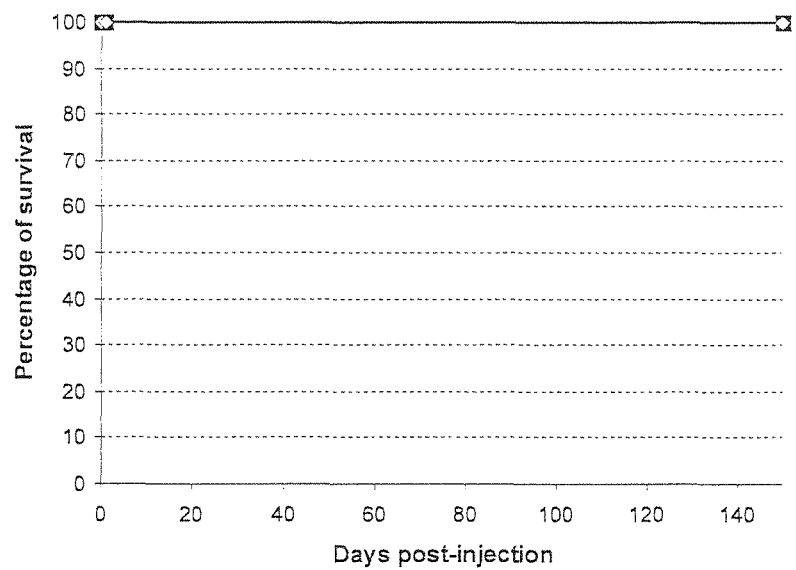
(B)
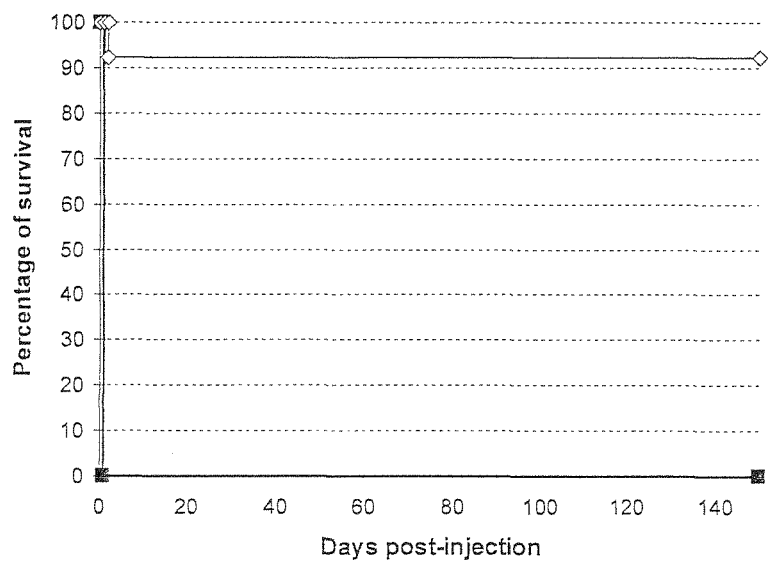
Figure 8

Figure 9
Day 13
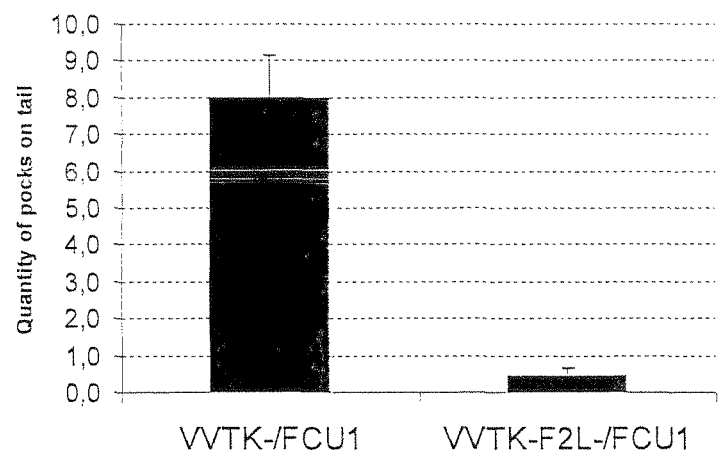
Day 34
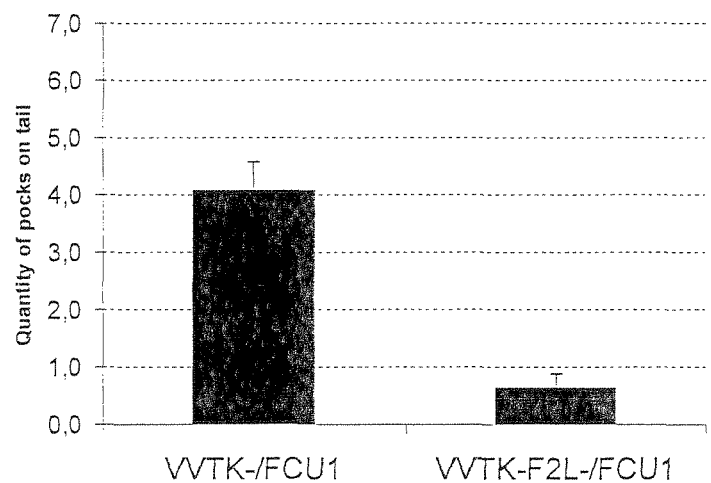

Figure 10

Day 15

[Bar chart: Number of pocks on tails; VVTK-/FCU1 ≈ 9.6; VVTK-F2L-/FCU1 ≈ 3.2]

Day 31

[Bar chart: Number of pocks on tails; VVTK-/FCU1 ≈ 6.7; VVTK-F2L-/FCU1 ≈ 3.5]

POXVIRAL ONCOLYTIC VECTORS

CROSS-REFERENCE TO PRIOR APPLICATIONS

This application claims priority under 35 U.S.C. §119 of EP 07301556.2, filed Nov. 19, 2007, and is a continuation of PCT/EP2008/009721, filed Nov. 17, 2008 and designating the United States (published in the English language on May 28, 2009, as WO 2009/065547 A3), each hereby expressly incorporated by reference in its entirety and each assigned to the assignee hereof.

TECHNICAL FIELD

Oncolytic viruses are a class of novel therapeutic agents used for the treatment of cancer that have the unique property of tumor-dependent self-perpetuation (HERMISTON. A demand for next-generation oncolytic adenoviruses. *Current opinion in molecular therapeutics.* 2006, vol. 8, no. 4, p. 322-30.). Oncolytic viruses are capable of selective replication in malignant cells and therefore offer levels of potency and specificity that are potentially far higher than conventional treatments for cancer (FISHER. Striking out at disseminated metastases: the systemic delivery of oncolytic viruses. *Current opinion in molecular therapeutics.* 2006, vol. 8, no. 4, p. 301-13.). The benefit of using these viruses is that as they replicate, they lyse their host cells. Cancer cells are ideal hosts for many viruses because they have the antiviral interferon pathway inactivated or have mutated tumour suppressor genes that enable viral replication to proceed unhindered (CHERNAJOVSKY, et al. Fighting cancer with oncolytic viruses. *British medical journal.* 2006, vol. 332, no. 7534, p. 170-2.).

Some viruses are naturally able to selectively replicate in tumoral cells but oncolytic viruses can also be obtained by modifying naturally occurring viruses. For this purpose, the main strategies used currently to modify the viruses include: functional deletions in essential viral genes; tumor- or tissue-specific promoters used to control the expression of these viral genes; and tropism modification to redirect adenovirus to the cancer cell surface. In the near future, oncolytic adenoviruses need to be optimized to fully realize their potential as critical anticancer tools and, thus, improve the prognosis for patients with malignant gliomas (JIANG, et al. Oncolytic adenoviruses as antiglioma agents. *Expert review of anticancer therapy.* 2006, vol. 6, no. 5, p. 697-708.).

For example, ONYX-015, an adenovirus modified selectively to replicate in and kill cells that harbor p53 mutations, is under development by Onyx Pharmaceuticals for the potential treatment of various solid tumors, including head and neck, gastrointestinal and pancreatic tumors. It is a recombinant adenovirus that carries a loss-of-function mutation at the E1B locus, the product of which is a 55 kDa protein that binds to and inactivates the p53 tumor suppressor protein. Thus, the ONYX-015 adenovirus is supposed to leave normal cells unaffected. Mutations in the p53 tumor suppressor gene are the most common type of genetic abnormality in cancer, occurring in more than half of all major cancer types. Thus, these cells are susceptible to the virus, which will readily replicate and cause cell death. ONYX-015 is in ongoing phase III trials for the treatment of recurrent head and neck cancer, phase II trials for colorectal, ovary, pancreas and mouth tumors, and phase I trials for digestive disease, esophagus and liver tumors (COHEN, et al. ONYX-015. Onyx Pharmaceuticals. *Current opinion in investigational drugs.* 2001, vol. 2, no. 12, p. 1770-5.).

Naturally oncolytic viruses are replication-competent viruses that have an innate ability to selectively infect and kill tumor cells. Despite being used in the original attempts to treat cancer with live viruses five decades ago, interest in naturally oncolytic viruses has lagged behind the support for engineered adenoviruses and herpesviruses as cancer therapeutics. Recently, however, there has been renewed interest in the high potency and selectivity of these naturally occurring agents (ROBERTS, et al. Naturally oncolytic viruses. *Current opinion in molecular therapeutics.* 2006, vol. 8, no. 4, p. 314-21.).

Among naturally oncolytic viruses, Vaccinia viruses (a Poxviridae) possess many of the key attributes necessary for an ideal viral backbone for use in oncolytic virotherapy. These include a short lifecycle, with rapid cell-to-cell spread. strong lytic ability, a large cloning capacity and well-defined molecular biology. In addition, although capable of replicating in human cells, they are not considered a natural health problem and are especially well characterized. having been delivered to millions of individuals during the campaign to eradicate smallpox. Early clinical results using either vaccine strains or genetically modified vaccinia strains have demonstrated antitumor effects (THORNE, et al. Vaccinia virus and oncolytic virotherapy of cancer. *Current opinion in molecular therapeutics.* 2005, vol. 7, no. 4, p. 359-65.).

In contrast, the poxvirus myxoma virus is a novel oncolytic candidate that has no history of use in humans directly, as it has a distinct and absolute host species tropism to lagomorphs (rabbits). Myxoma virus has been recently shown to be able to also selectively infect and kill human tumor cells, a unique tropism that is linked to dysregulated intracellular signalling pathways found in the majority of human cancers. This review outlines the existing knowledge on the tropism of myxoma virus for human cancer cells, as well as preclinical data exhibiting its ability to infect and clear tumors in animal models of cancer (STANFORD, et al. Myxoma virus and oncolytic virotherapy: a new biologic weapon in the war against cancer. *Expert opinion on biological therapy.* 2007, vol. 7, no. 9, p. 1415-25.).

Technical Problem

The injection of high doses of Poxviruses necessary to achieve an antitumoral effect raised toxicity issues. The majority of adverse events are minor, adverse reactions that are usually linked to Vaccinia virus are self-limited and include fever, headache, fatigue, myalgia, chills, local skin reactions, nonspecific rashes, erythema multiforme, lymphadenopathy, and pain at the vaccination site. Other reactions might require additional therapies (e.g., VIG, a first-line therapy and cidofovir, a second-line therapy). Adverse reactions that might require further evaluation or therapy include inadvertent inoculation, generalized vaccinia (GV), eczema vaccinatum (EV), progressive vaccinia (PV), postvaccinial central nervous system disease, and fetal vaccinia (CONO, et al. Smallpox vaccination and adverse reactions. Guidance for clinicians. *MMWR. Recommendations and reports: Morbidity and mortality weekly report. Recommendations and reports/Centers for Disease Control.* 2003, vol. 52, no. RR-4, p. 1-28.).

Thus, there is need for safer Poxviruses with an oncolytic activity as good as to their natural counterparts.

BACKGROUND ART

U.S. Pat. No. 5,364,773 (VIROGENETICS CORPORATION (TROY, N.Y.)) 15 Nov. 1994 describes a modified recombinant poxvirus, more particularly a vaccinia virus having inactivated nonessential virus-encoded encoded genetic functions so that the recombinant poxvirus has attenuated virulence and enhanced safety. In particular, the genetic functions are inactivated by deleting an open reading frame encoding a virulence factor or by insertional inactivation of an open reading frame encoding a virulence factor. More particularly, this patent describes a vaccinia virus in which the open reading frame of for J2R, B13R+B14R, A26L, A56R, C7L-K1L, and I4L has been inactivated. This virus (NYVAC) can be engineered as a vector for a foreign nucleic acid and used as a vaccine for inducing an immunological response in a host animal. However, N YVAC is unable to efficiently replicate in most mammalian cells and can not be used as an oncolytic virus (XIANGZHI, et al. Vaccinia virus K1L protein supports viral replication in human and rabbit cells through a cell-type-specific set of its ankyrin repeat residues that are distinct from its binding site for ACAP2. *Journal of virology.* 2006, vol. 353, no. 1, p. 220-233.).

WO 2004/014314 (KIRN DAVID (US)) 19 Feb. 2004 describes an altered vaccinia virus that comprises one or more mutations in its viral genome. Described mutations are in one or more of the following classes of polypeptides: 1) interferon-modulating polypeptide; 2) complement control polypeptide; 3) TNF or chemokine-modulating polypeptide; 4) serine protease inhibitor; 5) IL-lp modulating polypeptide; 6) non-infectious EEV form polypeptides; and, 7) viral polypeptide that act to inhibit release of infectious virus from cells (anti-infectious virus form polypeptide). In addition, mutations in A41L or C11R of vaccinia virus are also disclosed.

Vaccinia genome regions such as A34R, A41L, A53R, B5R, B7R, B8R, B13R, B15R, B18R, B22R, B28R, B29R, CUR, E3L, K2L, N1L, vC12L, and vCKBP are more particularly described in this application. Methods of the invention involve using any of the poxviruses discussed herein. The inventors also disclose methods to treat cancer by administering to the cancer cell or patient an effective amount of this altered vaccinia virus.

DISCLOSURE OF INVENTION

The inventors have surprisingly discovered that poxviruses comprising a defective F2L gene have an improved safety profile but kept an equivalent oncolytic activity (compared to their natural counterpart).

The present invention relates to a poxvirus comprising a defective F2L gene.

As used throughout the entire application, the terms "a" and "an" are used in the sense that they mean "at least one", "at least a first", "one or more" or "a plurality" of the referenced components or steps, unless the context clearly dictates otherwise. For example, the term "a cell" includes a plurality of cells, including mixtures thereof.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range.

As used herein, the terms "comprising" and "comprise" are intended to mean that the products, compositions and methods include the referenced components or steps, but not excluding others. "Consisting essentially of" when used to define products, compositions and methods, shall mean excluding other components or steps of any essential significance. Thus, a composition consisting essentially of the recited components would not exclude trace contaminants and pharmaceutically acceptable carriers. "Consisting of" shall mean excluding more than trace elements of other components or steps.

As used herein, the term "poxvirus comprising a defective gene" refers to a poxvirus comprising a deletion, substitution or addition in one or more nucleic acid of the defective gene, or any combination of these possibilities wherein said modifications lead to the inability for the virus to produce a protein having the activity of the protein produced by the unmodified gene. In a preferred embodiment of the invention, a poxvirus comprising a defective gene refers to a poxvirus in which the whole gene sequence has been deleted. Mutation can be made in a number of ways known to those skilled in the art using recombinant techniques. Methods for modifying the genome of a poxvirus are available in the art. For example the methods disclosed in MCCART, et al. Systemic cancer therapy with a tumor selective vaccinia virus mutant lacking thymidine kinase and vaccinia growth factor genes. *Cancer res.* 2001, no. 61, p. 8751-57., KIM, et al. Systemic armed oncolytic ans immunologic therapy for cancer with JX-594, a targeted poxvirus expressing GM-CSF. *Molecular Therapeutic.* 2006, no. 14, p. 361-70., WO 2004/014314 (KIRN DAVID (US)) 19 Feb. 2004 and U.S. Pat. No. 5,364,773 (VIROGENETICS CORPORATION (TROY, N.Y.)) 15 Nov. 1994 can be used to produce the poxvirus of the invention. The methods disclosed in the example of the present application are particularly relevant to produce a poxvirus according to the invention. Sequences of the genome of various poxviruses are available in the art, for example, the vaccinia virus, cowpox virus, Canarypox virus, Ectromelia virus, Myxoma virus genomes are available in Genbank (accession number NC_006998, NC_003663, NC_005309, NC_004105, NC_001132 respectively)

As used herein the term "poxvirus" refers to a virus belonging to the Poxviridae family. According to a preferred embodiment, the poxvirus according to the invention belongs to the Chordopoxvirinae subfamily, more preferably to the Orthopoxvirus genus and even more preferably to the Vaccinia virus specie.

For example, Vaccinia virus strains Dairen I, IHD-J, L-IPV, LC16M8, LC16MO, Lister, LIVP, Tashkent, WR 65-16, Wyeth, Ankara, Copenhagen, Tian Tan and WR can be used. According to a particularly preferred embodiment, the poxvirus according to the invention is a Vaccinia virus strains Copenhagen.

The poxvirus vaccinia contains a large duplex DNA genome (187 kilobase pairs) and is a member of the only known family of DNA viruses that replicates in the cytoplasm of infected cells. Because the infected cell must deliver large amounts of DNA precursors to cytoplasmic replication sites, the virus encodes and expresses many enzymatic activities required for DNA metabolism and synthesis, including deoxyuridine 5'-triphosphate nucleotidohydrolase (dUTPase).

Deoxyuridine 5'-triphosphate nucleotidohydrolase (dUTPase, EC 3.6.1.23) catalyzes the hydrolysis of dUTP to dUMP and pyrophosphate in the presence of $Mg(2+)$ ions. dUTPase, in removing dUTP from the dNTP pool and generating dUMP, is involved in both maintaining the fidelity of DNA replication and in proviging the precursor for the production of TMP by thymidylate synthase. Vaccinia dUTPase is a 15 kDa protein encoded by the F2L gene (MCGEOGH. *Nucleic Acids Research.* 1990, no. 18, p. 4105-10.; BROYLES. *Virology.* 1993, no. 195, p. 863-5.). Sequence of the F2L gene of the vaccinia virus is available in genbank via accession number M25392, sequences and locations of the F2L gene in various poxviruses genomes are also available in genbank, for example, via accession number NC_006998, DQ121394, NC_001611, AY689436, AY689437, NC_008291, DQ437594, DQ437593, AY313847, AY313848, NC_006966, NC_005309, NC_003391, NC_003389, NC_001132, NC_003310, NC_002188, M35027, AY243312, AF170726, DQ011157, DQ011156, DQ011155, DQ011154, DQ011153, X94355, Y16780, AY318871, U94848, AF198100 and M34368.

The gene nomenclature used herein is that of Copenhagen vaccinia strain and is used also for the homologous genes of other poxviridae unless otherwise indicated. However, gene nomenclature may be different according to the pox strain. For information, correspondance between Copenhagen and MVA genes can be found in Table I of ANTOINE. *Virology*. 1998, no. 244, p. 365-396.

According to a preferred embodiment, the poxvirus of the invention further comprises a defective J2R gene.

The J2R gene encodes a Thymidine kinase (TK) which form part of the salvage pathway for pyrimidine deoxyribonucleotide synthesis. The reaction catalysed by TK involves the transfer of a γ-phosphoryl moiety from ATP to 2'deoxythymidine (dThd) to produce thymidine 5'-monophosphate (dTMP). Vaccinia virus' TK is of type 2. Type 2 TKs have a smaller polypeptide chain compared to type 1, being of ~25 KDa but form homotetramers. They are sensitive to the feedback inhibitors dTDP or dTTP, which are generated at the end of the metabolic pathway. Type 2 TKs have a much narrower substrate specificity compared to type 1 TKs and only phosphorylate 2'deoxyuridine (dU) and/or dThd (EL OMARI, et al. Structure of vaccinia virus thymidine kinase in complex with dTTP: insights for drug design. *BMC structural biology*. 2006, no. 6, p. 22.).

Poxviruses defective for the J2R region and methods to obtain them are available in the art. For example, the teaching of MCCART, et al. Systemic cancer therapy with a tumor-selective vaccinia virus mutant lacking thymidine kinase and vaccinia growth factor genes. *cancer research*. 2001, vol. 61, no. 24, p. 8751-7., PUHLMANN, et al. Vaccinia as a vector for tumor-directed gene therapy: biodistribution of a thymidine kinase-deleted mutant. *Cancer gene therapy*. 2000, vol. 7, no. 1, p. 66-73., GNANT, et al. Systemic administration of a recombinant vaccinia virus expressing the cytosine deaminase gene and subsequent treatment with 5-fluorocytosine leads to tumor-specific gene expression and prolongation of survival in mice. *Cancer Research*. 1999, vol. 59, no. 14, p. 3396-403. can be used to produced a poxviruses deleted for the J2R region.

According to a preferred embodiment, the poxvirus according to the invention further comprises a nucleic acid of interest.

In a preferred embodiment, the nucleic acid of interest contains at least one sequence of interest encoding a gene product which is a therapeutic molecule (i.e. a therapeutic gene). A "therapeutic molecule" is one which has a pharmacological or protective activity when administered appropriately to a patient, especially patient suffering from a disease or illness condition or who should be protected against this disease or condition. Such a pharmacological or protective activity is one which is expected to be related to a beneficial effect on the course or a symptom of said disease or said condition. When the skilled man selects in the course of the present invention a gene encoding a therapeutic molecule, he generally relates his choice to results previously obtained and can reasonably expect, without undue experiment other than practicing the invention as claimed, to obtain such pharmacological property. According to the invention, the sequence of interest can be homologous or heterologous to the target cells into which it is introduced. Advantageously said sequence of interest encodes all or part of a polypeptide, especially a therapeutic or prophylactic polypeptide giving a therapeutic or prophylactic property. A polypeptide is understood to be any translational product of a polynucleotide regardless of size, and whether glycosylated or not, and includes peptides and proteins. Therapeutic polypeptides include as a primary example those polypeptides that can compensate for defective or deficient proteins in an animal or human organism, or those that act through toxic effects to limit or remove harmful cells from the body. They can also be immunity conferring polypeptides which act as endogenous antigen to provoke a humoral or cellular response, or both.

Examples of polypeptides encoded by a therapeutic gene include genes coding for a cytokine (alpha, beta or gamma interferon, interleukin, in particular IL-2, IL-6, IL-10 or IL-12, a tumor necrosis factor (TNF), a colony stimulating factor GM-CSF, C-CSF, M-CSF . . . ), a immunostimulatory polypeptide (B7.1, B7.2 and the like), a coagulation factor (FVIII, FIX . . . ), a growth factor (Transforming Growth Factor TGF, Fibroblast Growth Factor FGF and the like), an enzyme (urease, renin, thrombin, metalloproteinase, nitric oxide synthase NOS, SOD, catalase . . . ), an enzyme inhibitor (alpha1-antitrypsin, antithrombin III, viral protease inhibitor, plasminogen activator inhibitor PAI-1), the CFTR (Cystic Fibrosis Transmembrane Conductance Regulator) protein, insulin, dystrophin, a MHC antigen of class I or II, a polypeptide that can modulate/regulate expression of cellular genes, a polypeptide capable of inhibiting a bacterial, parasitic or viral infection or its development (antigenic polypeptides, antigenic epitopes, transdominant variants inhibiting the action of a native protein by competition . . . ), an apoptosis inducer or inhibitor (Bax, Bcl2, BclX . . . ), a cytostatic agent (p21, p 16, Rb . . . ), an apolipoprotein (ApoAI, ApoAIV, ApoE . . . ), an inhibitor of angiogenesis (angiostatin, endostatin . . . ), an angiogenic polypeptide (family of Vascular Endothelial Growth Factors VEGF, FGF family, CCN family including CTGF, Cyr61 and Nov), an oxygen radical scaveyer, a polypeptide having an anti-tumor effect, an antibody, a toxin, an immunotoxin and a marker (beta-galactosidase, luciferase . . . ) or any other genes of interest that are recognized in the art as being useful for the treatment or prevention of a clinical condition.

Suitable anti-tumor genes include but are not limited to those encoding tumor suppressor genes (e.g. Rb, p53, DCC, NF-1, Wilm's tumor, NM23, BRUSH-1, p16, p21, p56, p73 as well as their respective mutants), suicide gene products, antibodies, olypeptides inhibiting cellular division or transduction signals.

According to a particularly preferred embodiment, the poxvirus of the invention further comprises a suicide gene.

Suicide gene refers to a gene coding a protein able to convert a precursor of a drug into a cytoxic compound.

Suicide genes comprised but are not limited to genes coding protein having a cytosine deaminase activity, a thymidine kinase activity, an uracil phosphoribosyl transferase activity, a purine nucleoside phosphorylase activity and/or a thymidylate kinase activity.

Examples of Suicide genes and corresponding precursors of a drug comprising one nucleobase moiety are disclosed in the following table:

TABLE 1

| Suicide gene | predrug |
|---|---|
| Thymidine Kinase | Ganciclovir; |
| | Ganciclovir elaidic acid ester; |
| | penciclovir; |
| | Acyclovir; |
| | Valacyclovir; |
| | (E)-5-(2-bromovinyl)-2'-deoxyuridine; |
| | zidovudine; |
| | 2'-Exo-methanocarbathymidine |
| Cytosine deaminase | 5-Fluorocytosine |
| Purine nucleoside phosphorylase | 6-Methylpurine deoxyriboside; |
| | Fludarabine |
| uracil phosphoribosyl transferase | 5-Fluorocytosine; |
| | 5-Fluorouracil |
| thymidylate kinase. | Azidothymidine |

According to a preferred embodiment of the invention, the suicide gene codes a protein having at least a CDase activity. CDase is involved in the pyrimidine metabolic pathway by which exogenous cytosine is transformed into uracil by means of a hydrolytic deamination. While CDase activities have been demonstrated in prokaryotes and lower eukaryotes (JUND, et al. *Journal of Bacteriology*. 1970, no. 102, p. 607-15.; BECK, et al. *Journal of Bacteriology*. 1972, no. 110, p. 219-28.; HOEPRICH, et al. *Journal of Infectious Diseases*. 1974, no. 130, p. 112-18.; ESDERS, et al. *J. biol. chem.* 1985, no. 260, p. 3915-22.), they are not present in mammals (KO-ECHLIN, et al. *Biochemical pharmacology*. 1966, no. 15, p. 435-46.; POLAK, et al. *Chemotherapy*. 1976, no. 22, p. 137-53.).

CDase also deaminates an analogue of cytosine, i.e. 5-fluorocytosine (5-FC), thereby forming 5-fluorouracil (5-FU), which is a compound which is highly cytotoxic when it is converted into 5-fluoro-UMP (5-FUMP). Cells which lack CDase activity, either because of a mutation which inactivates the gene encoding the enzyme or because they are naturally deficient in this enzyme, as are mammalian cells, are resistant to 5-FC (JUND, et al. *Journal of Bacteriology*. 1970, no. 102, p. 607-15.; KILLSTRUP, et al. *Journal of Bacteriology*. 1989, no. 171, p. 2124-2127.). By contrast, mammalian cells into which the sequences encoding CDase activity were transferred became sensitive to 5-FC(HUBER, et al. *Cancer Research*. 1993, no. 53, p. 4619-4626.; MULLEN, et al. *Proceedings of the National Academy of Sciences of the United States of America*. 1992, no. 89, p. 33-37.; WO 93/01281 (US HEALTH)). In addition, the neighboring, untransformed cells also become sensitive to 5-FC (HUBER, et al. *Proceedings of the National Academy of Sciences of the United States of America*. 1994, no. 91, p. 8302-6.). This phenomenon, which is termed a bystander effect, is due to the cells which are expressing the CDase activity secreting 5-FU, which then intoxicates the neighboring cells by straightforward diffusion across the plasma membrane. This property of 5-FU in diffusing passively represents an advantage as compared with the tk/GCV reference system, where the bystander effect requires there to be contact with the cells which are expressing tk (MESNIL, et al. *Proceedings of the National Academy of Sciences of the United States of America*. 1996, no. 93, p. 1831-35.). All the advantages which CDase offers within the context of gene therapy, in particular anticancer gene therapy, can therefore be readily understood.

The *Saccharomyces cerevisiae* (*S. cerevisiae*) FCY1, *Candida Albicans* FCA1 and the *E. coli* codA genes, which respectively encode the CDase of these two organisms, are known and their sequences have been published (SEQ ID No:4; SEQ ID No:5; SEQ ID No:6 respectively).

With this respect, according to a more preferred embodiment of the invention, the gene coding a protein having a CDase activity is FCY1, FCA1 or CodA or an analogue thereof. Analogues of these genes refers to a gene having an nucleic acid sequence which have at least a degree of. identity greater than 70%, advantageously greater than 80%, preferably greater than 90%, and most preferably greater than 95% with the nucleic acid sequence of the parent gene.

Patent WO 2005/007857 discloses a gene coding a protein having an improved CDase activity. This polypeptides derived from a native CDase by addition of an amino acid sequence. According to another preferred embodiment of the invention, the protein having a CDase activity is a polypeptide disclosed WO 2005/007857 and more preferably the FCU1-8 polypeptide represented in the sequence identifier SEQ ID No:2 and analogues thereof.

In prokaryotes and lower eukaryotes, uracil is transformed into UMP by the action of uracil phosphoribosyl transferase (UPRTase). This enzyme converts 5-FU into 5-FUMP. According to another preferred embodiment of the invention, the suicide gene codes a protein having an UPRTase activity.

The UPRTase in question may be of any origin, in particular of prokaryotic, fungal or yeast origin. By way of illustration, the nucleic acid sequences encoding the UPRTases from *E. coli* (ANDERSEN, et al. Characterization of the upp gene encoding uracil phosphoribosyltransferase of *Escherichia coli* K12. *European Journal of Biochemistry*. 1992, no. 204, p. 51-56.), from *Lactococcus lactis* (MARTINUSSEN, et al. Cloning and characterization of upp, a gene encoding uracil phosphoribosyltransferase from *Lactococcus lactis*. *Journal of Bacteriology*. 1994, vol. 176, no. 21, p. 6457-63.), from *Mycobacterium bovis* (KIM, et al. Complete sequence of the UPP gene encoding uracil phosphoribosyltransferase from *Mycobacterium bovis* BCG. *Biochemistry and molecular biology international*. 1997, vol. 41, no. 6, p. 1117-24.) and from *Bacillus subtilis* (MARTINUSSEN, et al. Two genes encoding uracil phosphoribosyltransferase are present in *Bacillus subtilis*. *Journal of Bacteriology*. 1995, vol. 177, no. 1, p. 271-4.) may be used in the context of the invention. However, it is most particularly preferred to use a yeast UPRTase and in particular that encoded by the *S. cerevisiae* FUR1 gene whose sequence disclosed in KERN, et al. The FUR1 gene of *Saccharomyces cerevisiae*: cloning, structure and expression of wild-type and mutant alleles. *Gene*. 1990, vol. 88, no. 2, p. 149-57. is introduced here by way of reference. As a guide, the sequences of the genes and those of the corresponding UPRTases may be found in the literature and the specialist databanks (SWISSPROT, EMBL, Genbank, Medline and the like).

Application EP 0998568 A describes an FUR1 gene lacking 105 nucleotides in 5' of the coding part allowing the synthesis of a UPRTase from which the 35 first residues have been deleted at the N-terminal position and starting with the methionine at position 36 in the native protein. The product of expression of the mutant gene, designated FUR1Δ105, is capable of complementing an fur1 mutant of *S. cerevisiae*. In addition, the truncated mutant exhibits a higher UPRTase activity than that of the native enzyme. Thus, according to a particularly advantageous embodiment of the invention, the suicide gene codes a deletion mutant of a native UPRTase. The deletion is preferably located in the N-terminal region of the original UPRTase. It may be complete (affecting all the residues of said N-terminal region) or partial (affecting one or more continuous or discontinuous residues in the primary structure). In general, a polypeptide consists of N-terminal, central and C-terminal parts, each representing about a third of the molecule. For example, since the *S. cerevisiae*

UPRTase has 251 amino acids, its N-terminal part consists of the first 83 residues starting with the so-called initiator methionine situated at the first position of the native form. As for the *E. coli* UPRTase, its N-terminal part covers positions 1 to 69.

A preferred protein having an UPRTase activity comprises an amino acid sequence substantially as represented in the sequence identifier SEQ ID No: 1 of EP 0998568 A, starting with the Met residue at position 1 and ending with the Val residue at position 216. The term "substantially" refers to a degree of identity with said sequence SEQ ID No: 1 EP 0998568 A greater than 70%, advantageously greater than 80%, preferably greater than 90%, and most preferably greater than 95%. More preferably still, it comprises the amino acid sequence represented in the sequence identifier SEQ ID No: 1 EP 0998568 A. As mentioned above, it may comprise additional mutations. There may be mentioned in particular the substitution of the serine residue at position 2 (position 37 in the native UPRTase) by an alanine residue.

According to another preferred embodiment of the invention, the suicide gene codes a protein having at least one CDase and one UPRTase activity. Patent applications WO 96/16183 and EP 0998568 A describe the use of a fusion protein encoding an enzyme with two domains having the CDase and UPRTase activities and demonstrate that the transfer of a hybrid gene codA::upp or FCY1::FUR1 or FCY1::FUR1Δ105 (i.e. FCU1) carried by an expression plasmid increases the sensitivity of the transfected B16 cells to 5-FC. According to a more preferred embodiment of the invention, the suicide gene codes a polypeptide comprising an amino acid sequence substantially as represented in the sequence identifier SEQ ID No:3 (coda::upp), SEQ ID No:1 (FCU1) or FCY1::FUR1. The term "substantially" refers to a degree of identity with said sequence greater than 70%, advantageously greater than 80%, preferably greater than 90%, and most preferably greater than 95%. More preferably still, it comprises the amino acid sequence as represented in the sequence identifier SEQ ID No:3 (coda::upp), SEQ ID No:1 (FCU1) or FCY1::FUR1. As mentioned above, it may comprise additional mutations.

The nucleic acid sequences may be easily obtained by cloning, by PCR or by chemical synthesis according to the conventional techniques in use. They may be native genes or genes derived from the latter by mutation, deletion, substitution and/or addition of one or more nucleotides. Moreover, their sequences are widely described in the literature which can be consulted by persons skilled in the art.

Persons skilled in the art are capable of cloning the CDase or UPRTase sequences from the published data and of carrying out possible mutations, of testing the enzymatic activity of the mutant forms in an acellular or cellular system according to the prior art technology or based on the protocol indicated in application EP 0998568 A, and of fusing, in particular in phase, the polypeptides with CDase and UPRTase activity, and consequently all or part of the corresponding genes.

According to a more preferred embodiment, the poxvirus of the invention further comprises a nucleic acid sequence comprising a gene coding a permease.

Permease refers to transmembraneous protein involved in the transfer of a drug comprising one nucleobase moiety, or a precursor thereof through the cell membrane.

Permease comprises but are limited to purine permease, cytosine permease and nucleoside transporters.

According to a preferred embodiment of the invention, permease is a purine or a cytosine permease of *S. Cerevisiae*. The nucleobase transporters of *S. cerevisiae* consist of the purine-cytosine permease, known as FCY2, and the uracil permease, known as FUR4. The purine-cytosine permease, FCY2 mediates symport of protons and adenine, guanine, hypoxanthine and cytosine across the yeast plasma membrane (Grenson 1969, Jund and Lacroute 1970, Polak and Grenson 1973, Chevallier et al. 1975, Hopkins et al. 1988). FCY2 protein mediates also the transport of 5-fluorocytosine, an analogue of cytosine (Grenson 1969, Jund and Lacroute 1970). FCY2 gene encodes a protein of 533 amino acids (58 kDa) initially predicted to have 10-12 transmembrane— spanning domains (Weber et al. 1990), with nine now favoured (Ferreira et al. 1999). FCY2 exhibits similar affinities for the purine nucleobases and cytosine (Brethes et al. 1992). Uracil uptake into *S. cerevisiae* is mediated by the uracil permease, FUR4 (Jund and Lacroute 1970, Jund et al. 1977). FUR4 is a uracil-proton symporter (Hopkins et al. 1988) predicted to be a protein of 633 amino acids (71.7 kDa) with 10 transmembrane domains and long cytoplasmic hydrophylic N- and C-terminal tails (Jund et al. 1988, Garnier et al. 1996). FUR4 protein can also mediates the transport of 5-fluorouracil, an analogue of uracil (Jund and Lacroute 1970).

Amino acid sequences of FCY2 and Fur4 are notably available in the swissprot database (accession number P17064 and P05316 respectively). Preferably, permease has an amino acid sequence chosen from the group comprising amino acid sequence SEQ ID NO:1 and SEQ ID NO:2 as disclosed in patent application WO 2006/048768.

With this respect, according to a preferred embodiment of the invention, the permease is chosen from the group comprising FCY2 and Fur4 and analogues thereof. Analogues of Fur4 and FCY2 refers to polypeptide having an amino acid sequence which have at least a degree of identity greater than 70%, advantageously greater than 80%, preferably greater than 90%, and most preferably greater than 95% with the amino acid sequence of the parent protein as described here above and which retains the ability to transport a drug comprising one nucleobase moiety through the cell membrane.

The one skilled in the art is able to choose the permease which will be associated with the drug or the precursor of the drug comprising one nucleobase moiety. For example, FCY2 and Fur4 are preferably associated with 5-Fluorocytosine (5-FC).

According to a more preferred embodiment, the poxvirus of the invention may further comprise the elements necessary for the expression of the nucleic acid of interest.

According to a more preferred embodiment, the poxvirus of the invention may further comprise the elements necessary for the expression of the nucleic acid sequence comprising a gene coding a permease.

These elements necessary for the expression of the nucleic acid of interest and/or the nucleic acid sequence comprising a gene coding a permease comprised the elements required for transcription of said DNA into mRNA and, if necessary, for translation of mRNA into polypeptide. Transcriptional promoters suitable for use in various vertebrate systems are widely described in literature. For example, suitable promoters include viral promoters like RSV, MPSV, SV40, CMV or 7.5k, vaccinia promoter, inducible promoters, etc. Preferred promoters are isolated from poxviruses e.g. 7.5K, H5R, TK, p28, p11 or K1L of vaccinia virus. Alternatively, one may use a synthetic promoter such as those described in CHAKRABARTI. *Biotechniques*. 1997, no. 23, p. 1094-97., HAMMOND, et al. *Journal of Virological Methods*. 1997, no. 66, p. 135-38. and KUMAR. *Virology*. 1990, no. 179, p. 151-8. as well as chimeric promoters between early and late poxviral promoters.

The nucleic acid sequence of interest and the nucleic acid sequence comprising a gene coding a permease may further include additional functional elements, such as intron sequences, targeting sequences, transport sequences, secretion signal, nuclear localization signal, IRES, poly A transcription termination sequences, tripartite leader sequences, sequences involved in replication or integration. Said sequences have been reported in the literature and can be readily obtained by those skilled in the art.

The invention also relates to a process for preparing a poxvirus according to the invention, in which process:
(i) a poxvirus according to the invention is introduced into a cell,
(ii) said cell is cultured under conditions which are appropriate for enabling said poxvirus to be produced, and
(iii) said poxvirus is recovered from the cell culture.

While the poxvirus can of course be recovered from the culture supernatant, it can also be recovered from the cells. One of the commonly employed methods consists in lysing the cells by means of consecutive freezing/thawing cycles in order to collect the virions in the lysis supernatant. The virions can then be amplified and purified using the techniques of the art (chromatographic method, method of ultra-centrifugation, in particular through a cesium chloride gradient, etc.).

The present invention, also relates to a composition which comprises a poxvirus according to the invention in combination with a pharmaceutically acceptable excipient.

A composition according to the invention is more specifically intended for the preventive or curative treatment of diseases by means of gene therapy and is more specifically aimed at proliferative diseases (cancers, tumors, restenosis, etc.) or aimed at diseases associated to an increased osteoclast activity (e.g. rheumatoid arthritis, osteoporosis).

A composition according to the invention can be made conventionally with a view to administering it locally, parenterally or by the digestive route. In particular, a therapeutically effective quantity of the recombinant vector or poxvirus of the invention is combined with a pharmaceutically acceptable excipient. It is possible to envisage a large number of routes of administration. Examples which may be mentioned are the intragastric, subcutaneous, intracardiac, intramuscular, intravenous, intraperitoneal, intratumor, intranasal, intrapulmonary and intratracheal routes. In the case of these three latter embodiments, it is advantageous for administration to take place by means of an aerosol or by means of instillation. The administration can take place as a single dose or as a dose which is repeated on one or more occasions after a particular time interval. The appropriate route of administration and dosage vary depending on a variety of parameters, for example the individual, the disease to be treated or the gene(s) of interest to be transferred. The preparations based on viral particles according to the invention can be formulated in the form of doses of between $10^4$ and $10^{14}$ pfu (plaque-forming units), advantageously $10^5$ and $10^{13}$ pfu, preferably $10^6$ and $10^{12}$ pfu, more preferably $10^6$ and $10^7$.

The composition can also include a diluent, an adjuvant or an excipient which is acceptable from the pharmaceutical point of view, as well as solubilizing, stabilizing and preserving agents. In the case of an injectable administration, preference is given to a formulation in an aqueous, non-aqueous or isotonic solution. It can be presented as a single dose or as a multidose, in liquid or dry (powder, lyophilizate, etc.) form which can be reconstituted at the time of use using an appropriate diluent.

The present invention also relates to the use of a poxvirus or a composition according to the invention for preparing a medicament which is intended for treating the human or animal body by gene therapy. The medicament can be administered directly in vivo (for example by intravenous injection, into an accessible tumor, into the lungs by means of an aerosol, into the vascular system using an appropriate catheter, etc.). A preferred use consists in treating or preventing cancers, tumors and diseases which result from unwanted cell proliferation. Conceivable applications which may be mentioned are cancers of the breast, of the uterus (in particular those induced by papilloma viruses), of the prostate, of the lung, of the bladder, of the liver, of the colon, of the pancreas, of the stomach, of the oesophagus, of the larynx, of the central nervous system (e.g. glioblastoma) and of the blood (lymphomas, leukemia, etc.). An other preferred use consists in treating or preventing rheumatoid arthritis, osteoporosis and other diseases associated to an increased osteoclast activity. It can also be used in the context of cardiovascular diseases, for example in order to inhibit or retard the proliferation of the smooth muscle cells of the blood vessel wall (restenosis). Finally, in the case of infectious diseases, it is possible to conceive of the medicament being applied to AIDS.

When the poxvirus, composition or method of the invention is used for the treatment of cancer, the preferred route of administration is the systemic route since the poxvirus according to the invention is able to specifically target the tumoral cells.

The invention also extends to a method for treating diseases characterized in that a poxvirus, a composition according to the invention is administered to an host organism or cell which is in need of such treatment.

According to an advantageous embodiment, the therapeutic use or the treatment method also comprises an additional step in which pharmaceutically acceptable quantities of a prodrug, advantageously an analog of cytosine, in particular 5-FC, are administered to the host organism or cell. By way of illustration, it is possible to use a dose of from 50 to 500 mg/kg/day, with a dose of 200 mg/kg/day or of 100 mg/kg/day being preferred. Within the context of the present invention, the prodrug is administered in accordance with standard practice (e.g. per os, systematically).

Preferably, the administration taking place subsequent to the administration of the poxvirus or composition according to the invention, preferably at least 3 days, more preferably at least 4 days and even more preferably at least 5 days after the administration of the poxvirus or composition according to the invention. According to an even more preferred embodiment of the invention, the administration of the prodrug takes place 7 days after the administration of the therapeutic agent. The oral route is preferred. It is possible to administer a single dose of prodrug or doses which are repeated for a time which is sufficiently long to enable the toxic metabolite to be produced within the host organism or cell.

Furthermore, the composition or method according to the invention can be combined with one or more substances which potentiate the cytotoxic effect of the 5-FU. Mention may in particular be made of drugs which inhibit the enzymes of the pathway for the de novo biosynthesis of the pyrimidines (for example those mentioned below), drugs such as Leucovorin (Waxman et al., 1982, Eur. J. Cancer Clin. Oncol. 18, 685-692), which, in the presence of the product of the metabolism of 5-FU (5-FdUMP), increases the inhibition of thymidylate synthase, resulting in a decrease in the pool of dTMP, which is required for replication, and finally drugs such as methotrexate (Cadman et al., 1979, Science 250, 1135-1137) which, by inhibiting dihydrofolate reductase and increasing the pool of PRPP (phosphoribosylpyrophosphate), brings about an increase in the incorporation of 5-FU into the cellular RNA.

According to the present invention, the drugs which inhibit the enzymes of the pathway for the de novo biosynthesis of the pyrimidines are preferably selected from the group consisting of PALA (N-(phosphonoacetyl)-L-aspartate; Moore et al., 1982, Biochem. Pharmacol. 31, 3317-3321), Leflunomide, A771726 (active metabolite of Leflunomide; Davis et al., 1996, Biochem. 35, 1270-1273) and Brequinar (Chen et al., 1992, Cancer Res. 52, 3251-3257).

The composition or method according to the invention can be combined with one or more substances effective in anticancer therapy. Among pharmaceutical substances effective in anticancer therapy which may be used in association or in combination with the compositions according to the invention, there may be mentioned alkylating agents such as, e.g., mitomycin C, cyclophosphamide, busulfan, ifosfamide, isosfamide, melphalan, hexamethylmelamine, thiotepa, chlorambucil, or dacarbazine; antimetabolites such as, e.g., gemcitabine, capecitabine, 5-fluorouracil, cytarabine, 2-fluorodeoxy cytidine, methotrexate, idatrexate, tomudex or trimetrexate; topoisomerase II inhibitors such as, e.g., doxorubicin, epirubicin, etoposide, teniposide or mitoxantrone; topoisomerase I inhibitors such as, e.g., irinotecan (CPT-11), 7-ethyl-10-hydroxy-camptothecin (SN-38) or topotecan; antimitotic drugs such as, e.g., paclitaxel, docetaxel, vinblastine, vincristine or vinorelbine; and platinum derivatives such as, e.g., cisplatin, oxaliplatin, spiroplatinum or carboplatinum.

The compositions or methods according to the invention can also be use in combination with radiotherapy.

The compositions or methods according to the invention may also be use in combination with one or more other agents including but not limited to immunomodulatory agents such as, e.g. alpha, beta or gamma interferon, interleukin (in particular IL-2, IL-6, IL-10 or IL-12) or tumor necrosis factor; agents that affect the regulation of cell surface receptors such as, e.g. inhibitors of Epidermal Growth Factor Receptor (in particular cetuximab, panitumumab, zalutumumab, nimotuzumab, matuzumab, gefitinib, erlotinib or lapatinib) or inhibitors of Human Epidermal Growth Factor Receptor-2 (in particular trastuzumab); and agents that affect angiogenesis such as, e.g. inhibitor of Vascular Endothelial Growth Factor (in particular bevacizumab or ranibizumab).

BRIEF DESCRIPTION OF FIGURES IN THE DRAWINGS

FIG. 1. In vitro Sensitivities to 5-FC of vaccinia viruses infected human colorectal tumor cells (LoVo). LoVo cells, infected at a MOI of 0.0001 with the indicated viruses (mock (●) VVTK-/FCU1 (■) or VVTK-F2L-/FCU1 (◊)) were exposed to various concentration of 5-FC. Cell survival was measured at 5 days post-infection. Results were expressed in percentage of cellular viability in the presence or not of drugs. Values are represented in mean±SD of three individual determinations without the cell mortality due to the replication of the viruses.

Figure 2:
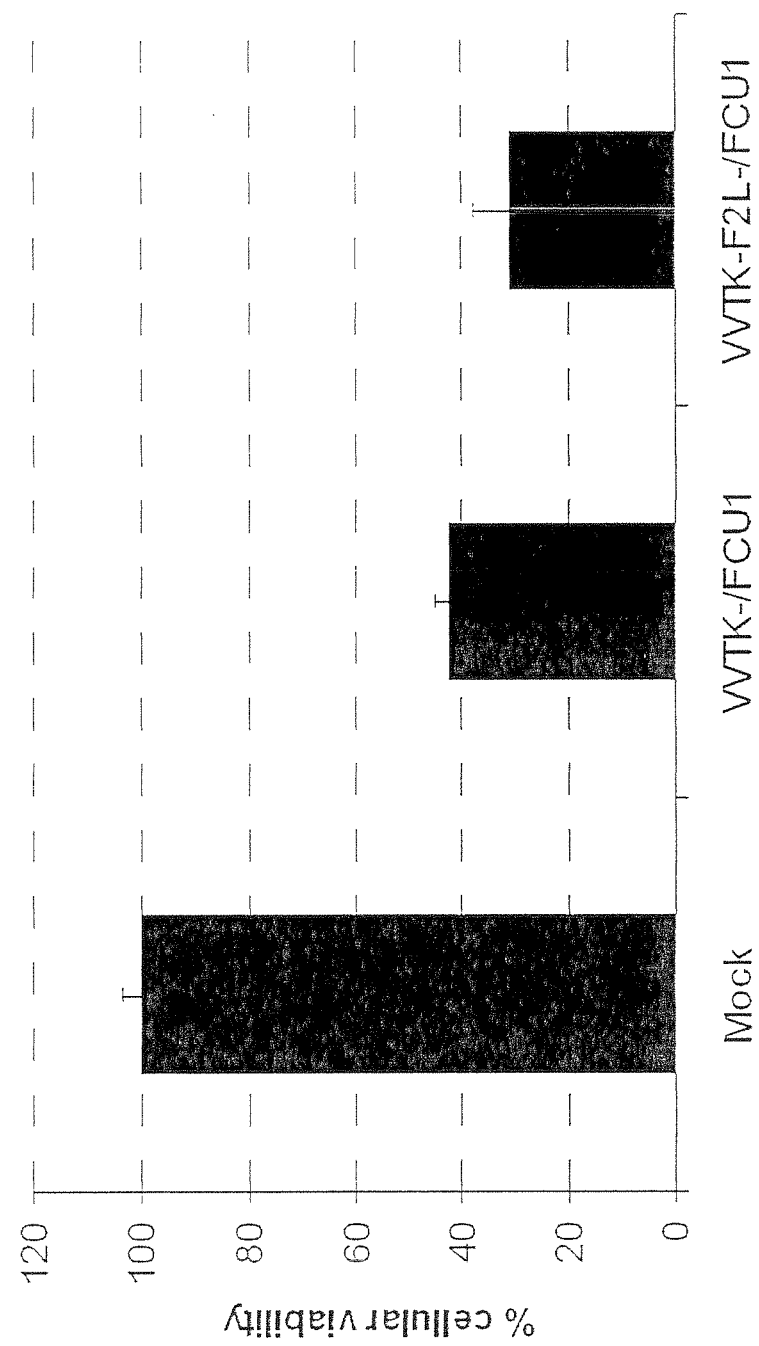

FIG. 2. In vitro replication efficacy of viruses in LoVo infected at a MOI of 0:0001 with the indicated viruses at day 5 post infection. Values are represented in mean±SD of three individual determinations.

Figure 3:
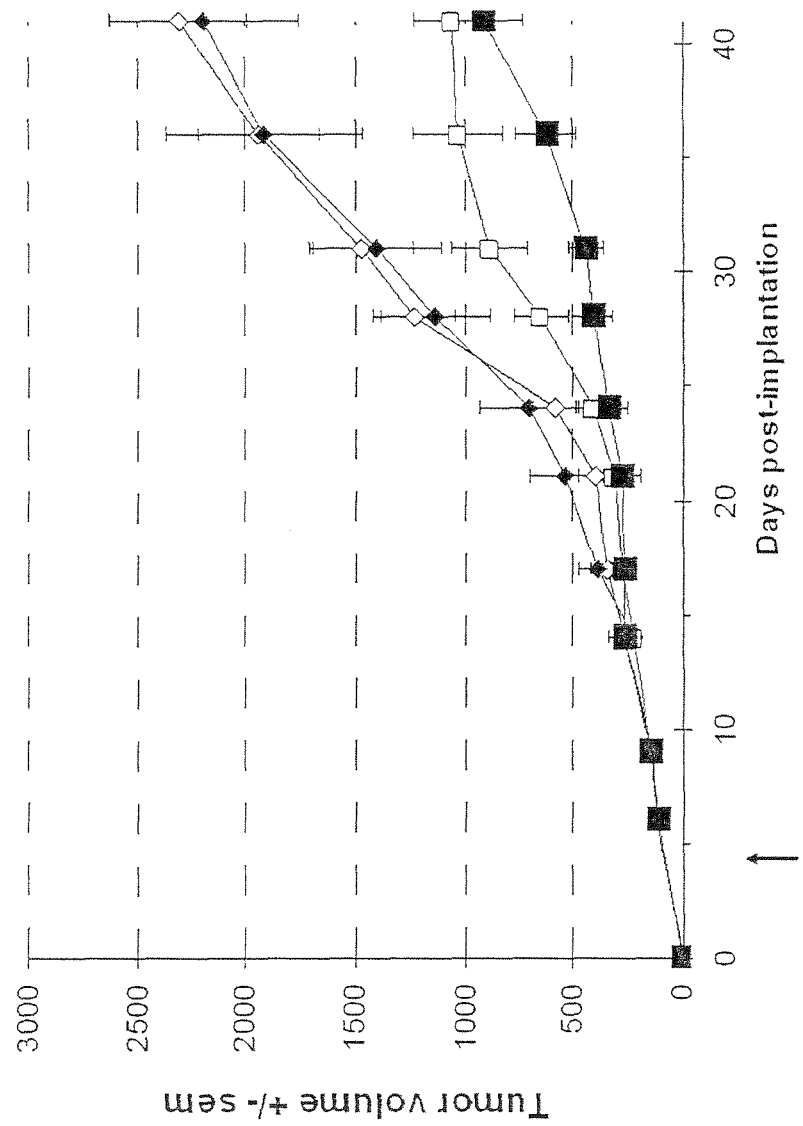

FIG. 3. Mean tumor volume±SEM of s.c LoVo in Swiss nude mice after i.v injection of virus. 7 days after inoculation with tumor (palpable tumor), mice were treated by $10^7$ pfu of buffer+saline (◊), buffer+5-FC (♦), VVTK-F2L-/FCU1+ saline (□) or VVTK-F2L-/FCU1+5-FC (■). The animals were treated by saline or 5-FC at 100 mg/kg/j twice a day by oral gavage, 7 days after virus injection during 3 weeks. Tumor volume was measured twice a week.

FIG. 4. Mean volume±SEM of s.c HepG2 tumors in Swiss nude mice after i.v injection of virus. 14 days after inoculation with tumors (palpable tumor), mice were treated by buffer+water (◊), or buffer+5-FC (♦), or $10^6$ pfu of VVTK-/FCU1+ water (○), or $10^6$ pfu of VVTK-/FCU1+5-FC (●) (A); or water (○), or buffer+water (◊), or buffer+5-FC (♦) or $10^6$ pfu of VVTK-F2L-/FCU1+water (◊), or $10^6$ pfu of VVTK-F2L-/FCU1+5-FC (♦) (B). The animals were treated by 5-FC at 100 mg/kg twice a day by oral gavage, 7 days after virus injection and during 3 weeks. Tumor volume was measured twice a week.

Figure 5:
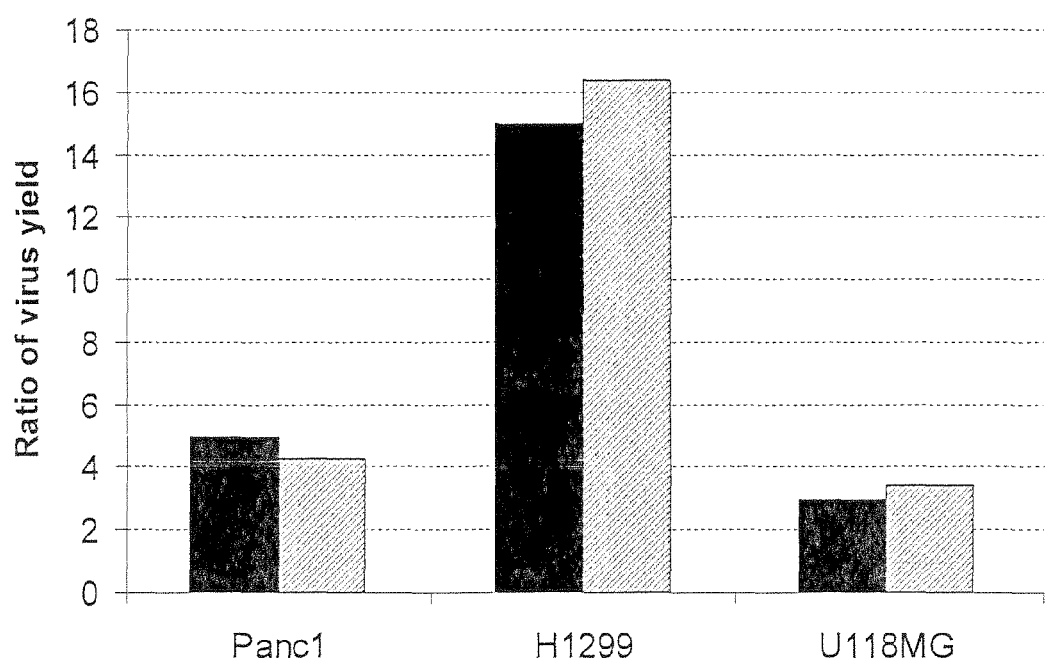

FIG. 5. Ratio of virus yield in dividing cells versus in confluent cells. PANC1 (pancreatic human tumor), H1299 (Lungs human tumor) or U118MG (glioma human tumor) cells are infected with 100 pfu of (■) VVTK-/FCU1 or (□) VVTK-F2L-/FCU1. 48h post-infection, viral titers were determined. Values are the ratio between yields of virus in dividing cells versus in confluent cells.

Figure 6:
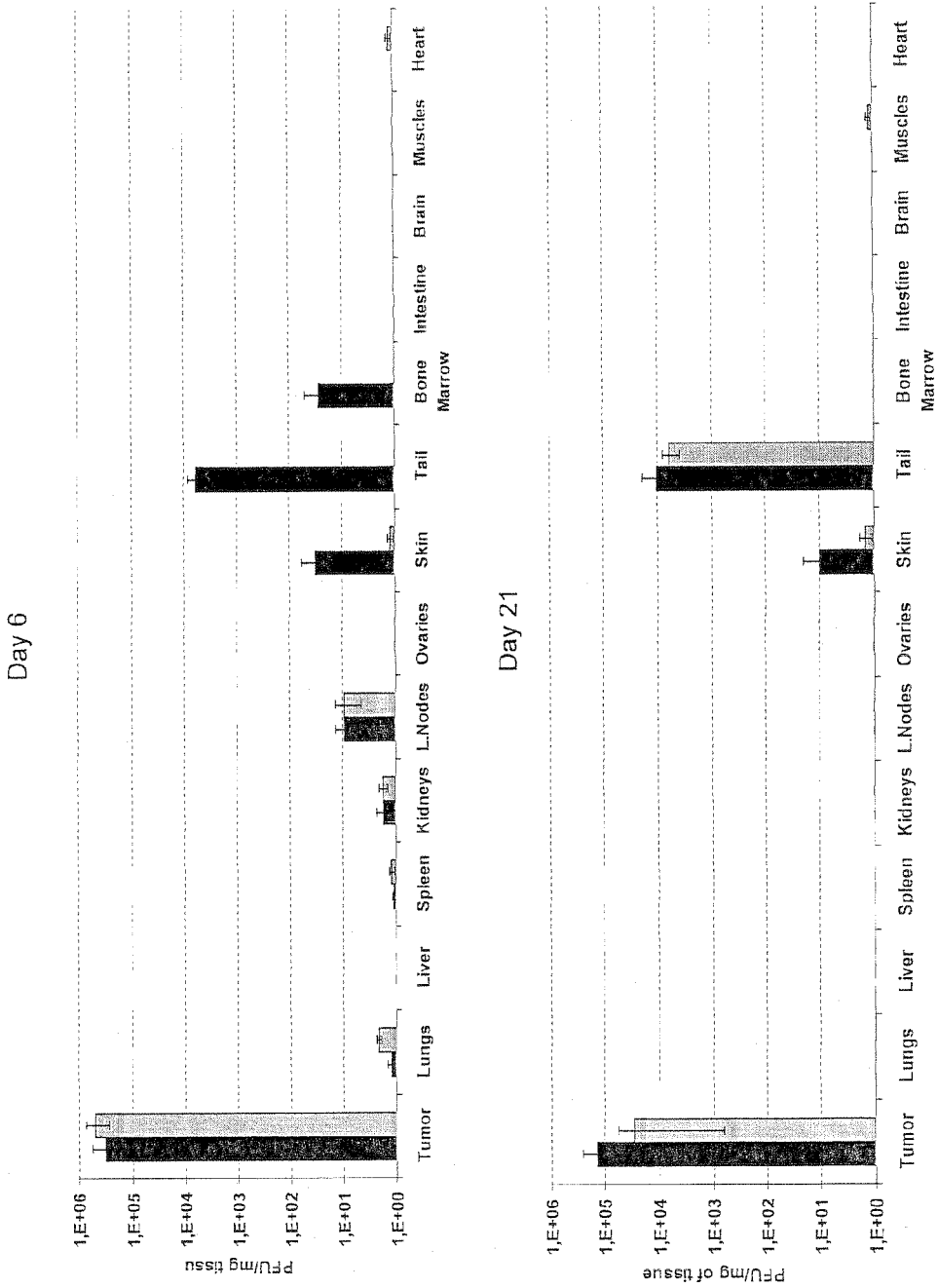

FIG. 6. Viral titers (pfu/mg of tissue) in organs or tumors at day 6 and day 21 after i.v. infection into Swiss nude mice bearing subcutaneous human tumors with $1\times10^6$ PFU of VVTK-/FCU1 (■) or VVTK-F2L-/FCU1 (□).

Figure 7:
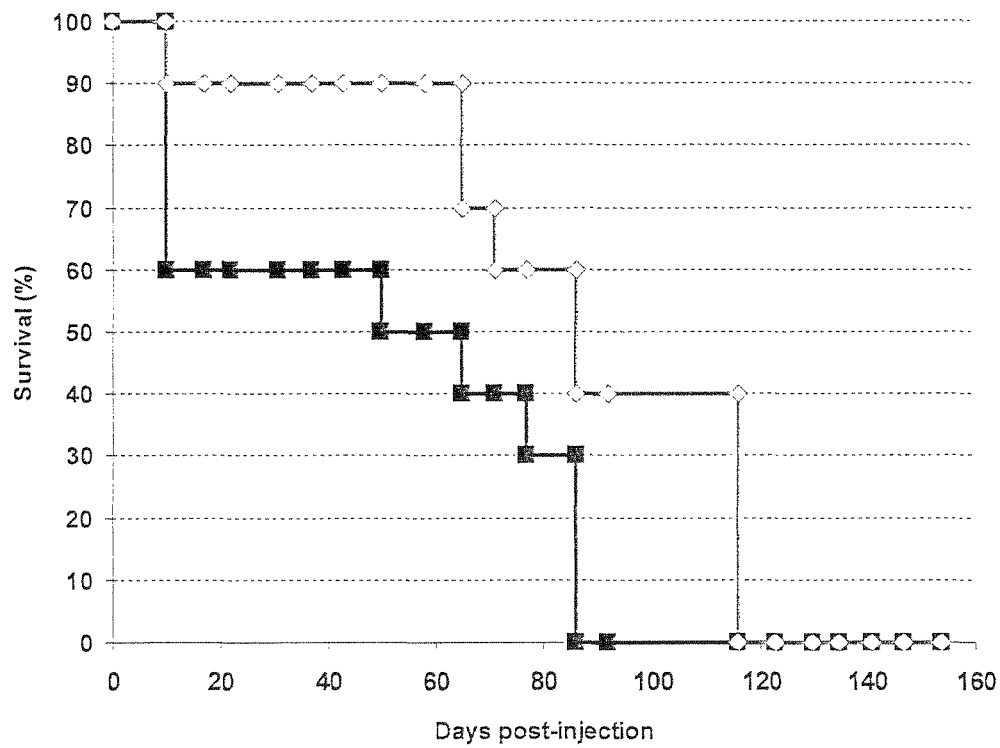

FIG. 7. Survival of Swiss nude mice after treatment with $1\times10^8$ pfu of VVTK-/FCU1 (■) or VVTK-F2L-/FCU1 (◊) by i.v injection.

FIG. 8. Survival of immunocompetent B6D2 mice after treatment with $1\times10^7$ pfu (A) or $1\times10^8$ pfu (B) of VVTK-/FCU1 (■) or VVTK-F2L-/FCU1 (◊) by i.v injection.

FIG. 9. Average quantity of pocks on tails after i.v injection of $1\times10^6$ pfu VVTK-/FCU1 or VVTK-F2L-/FCU1 in Swiss nude mice at day 13 post-infection and at day 34 post-infection.

FIG. 10. Average quantity of pocks on tails after i.v injection of $1\times10^7$ pfu VVTK-/FCU1 or VVTK-F2L-/FCU1 in Swiss nude mice at day 15 post-infection and at day 31 post-infection.

MODE(S) FOR CARRYING OUT THE INVENTION

Examples

Construction of Vector Plasmids

A shuttle plasmid for deleting F2L was constructed using the DNA of vaccinia virus strain Copenhagen (accession number M35027). The DNA flanking regions of F2L were amplified by PCR. Primers of the upstream flanking region of F2L were 5'-CGC GGATCC GAA AGC GAT GAA CTA AAT GTT C-3' (SEQ ID No:7; BamHI site underlined) and 5'-TCC CCCGGG GTT AGT TTC CTT AAC AAA TCT AAC-3' (SEQ ID No:8; SmaI site underlined). Primers for the downstream region were 5'-GCC TGG CCA ACA AAT AGA GGA GAT CAA GGG T-3' (SEQ ID No:9; MscI site underlined) and 5'-GCC CAGCTG ACC ACT ACA TCA ATT TTA CAA AAG-3' (SEQ ID No:10; PvuII site underlined). The amplified DNA fragment were digested with restriction enzyme SmaI/BamHI or MscI/PvuII and ligated into the corresponding sites in PpolyIII plasmid. A repeat region of the downstream flanking region of F2L was amplified by PCR using the primers 5'-GCC GCATGC TCC AGA ATT GAT CAT AGT GGA TA-3' (SEQ ID No:11; SphI site underlined) and 5'-GCTCTAGA G TTA GTT TCC TTA ACA AAT CTA AC-3' (SEQ ID No:12; XbaI site underlined) and inserted in PpolyIII plasmid. The repeat region is used to eliminate the selection cassette during the production of deleted viruses. The selection cassette, corresponding to the GFP/GPT fusion gene under the control of pH5R vaccinia promoter, was inserted into the SmaI/SphI site in PpolyIII plasmid. The obtained plasmid is the recombinant shuttle plasmid named pΔF2L for deletion of F2L gene.

The Generation of Recombinant Vaccinia Viruses.

CEF cells were infected with VVTK-FCU1(Vaccinia virus, defective for the J2R gene, expressing FCU1 gene under the control of synthetic promoter p11k7.5) strain Copenhagen at a MOI of 0.1 and incubated at 37° C. for 2 h, then transfected with a CaCl$_2$ coprecipitate of the recombinant shuttle plasmid (0.2 µg). The cells were incubated for 48 h at 37° C. Dilutions of virus emerging were then used to infect the CEF cells in selection medium containing Hypoxanthine at final concentration of 15 µg/ml xanthine at final concentration of 250 µg/ml and mycophenolic acide at final concentration of 250 µg/ml. Fluorescent (GFP) and positive (GPT selection) plaques were isolated and selected for a several round of selection in CEF cells in presence of GPT selection medium. The presence or not of VVTk-FCU1 was determined by 40 cycles of PCR with primers inside the deletion region. After the elimination of parental virus, the double deleted virus was used to infect CEF without GPT selection medium to eliminate the selection cassette. Nonfluorescent plaques were isolated and selected for 2 cycles in CEF. Final recombinant VV viruses were amplified in CEF, purified and virus stocks were titrated on CEF by plaque assay.

In vitro Cell Sensitivity to 5-FC.

Human tumor cells were transduced by the respective recombinant VV at a MOI of 0.0001. A total of $3 \times 10^5$ cells/well were plated in 6-well culture dishes in 2 ml of medium containing various concentrations of 5-FC. Cells were then cultured at 37° C. for 5 days, and the viable cells were counted by trypan blue exclusion. Results depicted in FIG. 1 and FIG. 2 shows that the FCU1 activity is equivalent in viruses defective for the J2R gene than in virus defective for the J2R and F2L gene.

In Vitro Replication in Cultured Cells.

Dividing or confluent cells were infected, in 6-wells plaques, at 100 PFU of viruses (nearly MOI 0.0005). 2 mL of medium supplemented with 10% FCS for dividing cells and no supplemented for confluent cells were added. The cells were harvested at 48 hours post-infection. The cells were stored at −20° C. and sonicated to release the virus, virus was also quantified by plaque titration on CEF cells. The ratio between replication in dividing cells and confluent cells are similar in all cells. Both viruses VVTK-/FCU1 and VVTK-F2L-/FCU1 replicate more in dividing cells than in confluent cells.

As an indirect mean to assay for replication virus specificity, the yield of virus produced in dividing versus confluent tumor cells (pancreatic human tumor PANC1; lung human tumor H1299; glioma human tumor U118MG) was determined. Confluent cells were plated at $1 \times 10^6$ cells/well and cultured in complete media for 7 days then 1 day before infection the cells were washed and cultured in media without serum. Dividing cells were plated at $3 \times 10^5$ cells/well one day before infection. To evaluate the level of cell division, the amount of titrated thymidine incorporated into nucleic acid was measured 5 hours, 24 hours and 48 hours after plating cells. During this period thymidine incorporation was relatively constant in confluent cells whereas in dividing cells an increase in incorporation was seen over time. Then the cells were infected with 100 pfu of viruses, and 48 h post infection the ratio between the yield of virus produced in dividing tumor cells and in confluent tumor cells was determined by plaque titration on CEF. Results depicted in FIG. 5 show that both viruses VVTK-/FCU1 and VVTK-F2L-/FCU1 replicate more in dividing cells than in confluent cells.

Subcutaneous Tumor Model.

Female Swiss nude mice were obtained from Charles River Laboratories. Animals used in the studies were uniform in age (6 weeks) and body weights ranged from 20-23 g. Swiss nude mice were injected subcutaneously (s.c.) into the flank with $5 \times 10^6$ LoVo cells/100 µL. When tumors reached a diameter of 50-70 mm$^3$, the mice were randomized in a blinded manner and treated with the indicated vectors for the in vivo experiments.

Biodistribution of the Virus.

The presence of VV-FCU1 and VVTK-F2L-/FCU1 was evaluated by virus titration in tumors and organ samples. $1 \times 10^6$ PFU of the viruses was injected intravenously (i.v.) by tail vein injection into nude mice bearing established s.c. LoVo tumors. Mice were sacrificed at day 14 post-infection, and the tumors and other organs were collected and weighted. Tumors and organs were homogenized in PBS and titers were determined on CEF as described previously. Viral titers were standardized to milligram of tissue. Results depicted in Table 2 and 3 (The range of virus titers is presented in pfu/mg of tissue) show that after 14 days the virus according to the invention is mostly found in the tumor. In a second set of experimentations according to the same conditions as described above, mice were sacrificed at day 6 and 21 post-infection. Results depicted in FIG. 6 show that both viruses VVTK-/FCU1 and VVTK-F2L-/FCU1 target the tumor with about 1 000 to 10 000 fold more virus in the tumor than in the other organs analyzed except for tails in the case of VVTK-/FCU1. A small amount of VVTK-/FCU1 is detected in lungs, spleen, kidney and lymph nodes (less than 10 pfu/mg) and more in skin, tail and bone marrow at day 6, and skin and tail at day 21. In contrast, VVTK-F2L-/FCU1 has higher tumor specificity with only a small amount in lungs, spleen, kidney, lymph nodes and skin at day 6, and in skin and tail at day 21.

TABLE 2

|  | Tumor | Lungs | Spleen | Kidney | Heart | L. Nodes |
|---|---|---|---|---|---|---|
| VVTK-/FCU1 | $(0.2\text{-}3.3) \times 10^5$ | 0.1-2 | 0-2.2 | 0-1.8 | 0-0.3 | 0-61 |
| VVTK-F2L/FCU1 | $0\text{-}8.1 \times 10^4$ | 0-5.7 | 0-9.3 | 0.2-3 | 0.2 | 0-83 |

TABLE 3

|  | Ovaries | Skin | Tail | Bone Marrow | Brain | Muscles | Heart |
|---|---|---|---|---|---|---|---|
| VVTK-/FCU1 | 2.2-74 | 0.1-24 | $13.5\text{-}7.10^4$ | 0-800 | 0-1.8 | 0-22 | 0-0.3 |
| VVTK-F2L/FCU1 | 0-108 | 0-88 | 0.8-16.3 | n.d | 0-0.2 | 0-1.8 | 0.2 |

Antitumor Activity of the Poxvirus of the Invention in S.C. Tumor Model.

Nude mice bearing established s.c. LoVo tumors (50-70 mm$^3$) were treated one time intratumorally or two times intravenously (by tail vein) with the indicated vectors at dose of $1.10^4$ PFU, $1.10^6$ or $1.10^7$ PFU, respectively. Starting day 7 following viral injection, 5-FC was given by oral gavage at 100 mg/kg (0.5 ml 5-FC 0.5% in water) twice a day for 3 weeks. Tumor size was measured twice weekly using calipers. Tumor volume were calculated in mm³ using the formula (p/6) (length×width²). The results depicted in FIG. 3 show that the 2 viruses have a similar efficacy with an oncolytic activity (p<0.05) able to control the growth of tumor, and a combined activity (oncolytic of the virus and therapeutic of FCU1 gene) with administration of 5-FC which can further improve the control of the tumor growth (p<0.01).

Nude mice bearing established s.c. HepG2 (Human hepatocellular liver carcinoma cells) were treated intravenously (by tail vein) with the indicated vectors at dose of 1.10⁶ PFU according to the followings: 14 days after inoculation with tumors (palpable tumor), mice were treated by buffer+water, or buffer+5-FC, or 10⁶ pfu of VVTK-/FCU1+water, or 10⁶ pfu of VVTK-/FCU1+5-FC, or 10⁶ pfu of VVTK-F2L-/FCU1+water, or 10⁶ pfu of VVTK-F2L-/FCU1+5-FC. The animals were treated by 5-FC at 100 mg/kg twice a day by oral gavage, 7 days after virus injection and during 3 weeks. Tumor size was measured twice weekly using calipers. Tumor volume were calculated in mm³ using the formula (π/6) (length×width²). The results depicted in FIG. 4 show that tumor progression is controlled after VVTK-/FCU1 and VVTK-F2L-/FCU1 injection (p<0.0005) compared to buffer. The activity is not enhanced with administration of 5-FC. The virus oncolytic activity alone is very potent with only 1×10⁶ pfu of viruses injected.

Viral Pathogenicity.

Viral pathogenicity was assessed with survival studies done on both Swiss nude mice (FIG. 7) and immunocompetents B6D2 mice (6 weeks from Charles Rivers) (FIG. 8). Mice were injected I.V. with 1.10⁷ or 1.10⁸ PFU of all viruses in 100 μL of Buffer per mouse. Mice were observed daily throughout the course of the experiment. In Swiss nude mice (FIG. 7), the injection of 1×10⁸ PFU of VVTK-/FCU1 results in the death of 40% of the animals 3 days after infection. The remaining mice died between day 50 and day 80 after infection. The administration of VVTK-F2L-/FCU1 was less pathogenic, the majority of the animals died between day 65 to 115 (p<0.05). No evidence of toxicity has been observed with both viruses at 10⁷ pfu. All mice died after i.v injection of 10⁸ pfu of VVTK-/FCU1. The group with treatment of VVTK-F2L-/FCU1 had significantly prolonged survival to 92% (p<0.00005) compared with the VVTK-/FCU1 infected mice. Therefore, this result demonstrates the decrease of toxicity with the double-deleted virus VVTK-F2L-/FCU1.

Pocks Tail Lesion Model.

Swiss nude mice were injected I.V. with 1.10⁶ (FIG. 9) or 1.10⁷ PFU (FIG. 10) of each virus. Tail lesions were enumerated once a week. Mice injected with 1.10⁶ PFU of VVTK-F2L-/FCU1 have less than 1 pocks/mice compared with mice injected with VVTK-/FCU1 with a average of 8 pocks by mice in day 13 post-infection (p<0.001) as shown in FIG. 9 (A). The results are similar at day 34 post-injection with an average of 4 pocks with VVTK-/FCU1 compared to nearly 1 for VVTK-F2L-/FCU1 (p<0.0001) as shown in FIG. 9 (B). Mice injected with 1.10⁷ PFU of VVTK-F2L-/FCU1 have respectively an average of 3.5 pocks/mice compared to mice injected with 1.10⁷ PFU of VVTK-/FCU1 having an average of 10 pocks/mice at day 15 post-infection (FIG. 10 (A)). At day 31 post-infection mice injected with VVTK-F2L-/FCU1 have respectively an average of 3.5 pock/mice compared to mice injected with VVTK-/FCU1 having an average of 7 pocks/mice (FIG. 10 (B)). The difference in pock number between VVTK-/FCU1 and VVTK-F2L-/FCU1 is statistically significant (p<0.05). The pocks formation is correlated with the replication of virus in the tail and so with virulence and toxicity. Injection in i.v of VVTK-F2L-/FCU1 is less toxic than with the single deleted TK virus.

Statistical Analysis.

Statistical analyses were performed using the nonparametric Mann-Whitney U test and STATISTICA 7.1 software (StatSoft, Inc.). A P<0.05 was considered to be statistically significant.

REFERENCES

U.S. Pat. No. 5,364,773 (VIROGENETICS CORPORATION (TROY, N.Y.)) 15 Nov. 1994
WO 2004/014314 (KIRN DAVID (US)) 19 Feb. 2004
WO 2004/014314 (KIRN DAVID (US)) 19 Feb. 2004
U.S. Pat. No. 5,364,773 (VIROGENETICS CORPORATION (TROY, N.Y.)) 15 Nov. 1994
WO 93/01281 (US HEALTH)
WO 2005/007857
WO 2005/007857
EP 0998568 A
EP 0998568 A
EP 0998568 A
EP 0998568 A
WO 96/16183
EP 0998568 A
EP 0998568 A
WO 2006/048768
HERMISTON. A demand for next-generation oncolytic adenoviruses. *Current opinion in molecular therapeutics*. 2006, vol. 8, no. 4, p. 322-30.
FISHER. Striking out at disseminated metastases: the systemic delivery of oncolytic viruses. *Current opinion in molecular therapeutics* 2006, vol. 8, no. 4, p. 301-13.
CHERNAJOVSKY, et al. Fighting cancer with oncolytic viruses. *British medical journal*. 2006, vol. 332, no. 7534, p. 170-2.
JIANG, et al. Oncolytic adenoviruses as antiglioma agents. *Expert review of anticancer therapy*. 2006, vol. 6, no. 5, p. 697-708.
COHEN, et al. ONYX-015. Onyx Pharmaceuticals. *Current opinion in investigational drugs*. 2001, vol. 2, no. 12, p. 1770-5.
ROBERTS, et al. Naturally oncolytic viruses. *Current opinion in molecular therapeutics*. 2006, vol. 8, no. 4, p. 314-21.
THORNE, et al. Vaccinia virus and oncolytic virotherapy of cancer. *Current opinion in molecular therapeutics*. 2005, vol. 7, no. 4, p. 359-65.
STANFORD, et al. Myxoma virus and oncolytic virotherapy: a new biologic weapon in the war against cancer. *Expert opinion on biological therapy*. 2007, vol. 7, no. 9, p. 1415-25.
CONO, et al. Smallpox vaccination and adverse reactions. Guidance for clinicians. *MMWR. Recommendations and reports: Morbidity and mortality weekly report. Recommendations and reports/Centers for Disease Control*. 2003, vol. 52, no. RR-4, p. 1-28.
XIANGZHI, et al. Vaccinia virus K1L protein supports viral replication in human and rabbit cells through a cell-type-specific set of its ankyrin repeat residues that are distinct from its binding site for ACAP2. *Journal of virology*. 2006, vol. 353, no. 1, p. 220-233.
MCCART, et al. Systemic cancer therapy with a tumor selective vaccinia virus mutant lacking thymidine kinase and vaccinia growth factor genes. *Cancer res*. 2001, no. 61, p. 8751-57.

KIM, et al. Systemic armed oncolytic ans immunologic therapy for cancer with JX-594, a targeted poxvirus expressing GM-CSF. *Molecular Therapeutic.* 2006, no. 14, p. 361-70.

SLABAUGH, et al. *Journal of virology.* 1988, vol. 62, p. 519-27.

TENGELSEN, et al. *Virology.* 1988, no. 164, p. 121-31.

SCHMITT, et al. *Journal of virology.* 1988, no. 62, p. 1889-97.

SLABAUGH, et al. *Journal of virology.* 1984, no. 52, p. 507-14.

SLABAUGH, et al. *Journal of virology.* 1984, no. 52, p. 501-6.

HOWELL, et al. *Journal of Biological Chemistry.* 1992, no. 267, p. 1705-11.

MCGEOGH. *Nucleic Acids Research.* 1990, no. 18, p. 4105-10.

BROYLES. *Virology.* 1993, no. 195, p. 863-5.

ANTOINE. *Virology.* 1998, no. 244, p. 365-396.

EL OMARI, et al. Structure of vaccinia virus thymidine kinase in complex with dTTP: insights for drug design. *BMC structural biology.* 2006, no. 6, p. 22.

MCCART, et al. Systemic cancer therapy with a tumor-selective vaccinia virus mutant lacking thymidine kinase and vaccinia growth factor genes. *cancer research.* 2001, vol. 61, no. 24, p. 8751-7.

PUHLMANN, et al. Vaccinia as a vector for tumor-directed gene therapy: biodistribution of a thymidine kinase-deleted mutant. *Cancer gene therapy.* 2000, vol. 7, no. 1, p. 66-73.

GNANT, et al. Systemic administration of a recombinant vaccinia virus expressing the cytosine deaminase gene and subsequent treatment with 5-fluorocytosine leads to tumor-specific gene expression and prolongation of survival in mice. *Cancer Research.* 1999, vol. 59, no. 14, p. 3396-403.

JUND, et al. *Journal of Bacteriology.* 1970, no. 102, p. 607-15.

BECK, et al. *Journal of Bacteriology.* 1972, no. 110, p. 219-28.

HOEPRICH, et al. *Journal of Infectious Diseases.* 1974, no. 130, p. 112-18.

ESDERS, et al. *J. biol. chem.* 1985, no. 260, p. 3915-22.

KOECHLIN, et al. *Biochemical pharmacology.* 1966, no. 15, p. 435-46.

POLAK, et al. *Chemotherapy.* 1976, no. 22, p. 137-53.

JUND, et al. *Journal of Bacteriology.* 1970, no. 102, p. 607-15.

KILLSTRUP, et al. *Journal of Bacteriology.* 1989, no. 171, p. 2124-2127.

HUBER, et al. *Cancer Research.* 1993, no. 53, p. 4619-4626.

MULLEN, et al. *Proceedings of the National Academy of Sciences of the United States of America.* 1992, no. 89, p. 33-37.

HUBER, et al. *Proceedings of the National Academy of Sciences of the United States of America.* 1994, no. 91, p. 8302-6.

MESNIL, et al. *Proceedings of the National Academy of Sciences of the United States of America.* 1996, no. 93, p. 1831-35.

ANDERSEN, et al. Characterization of the upp gene encoding uracil phosphoribosyltransferase of *Escherichia coli* K12. *European Journal of Biochemistry.* 1992, no. 204, p. 51-56.

MARTINUSSEN, et al. Cloning and characterization of upp, a gene encoding uracil phosphoribosyltransferase from *Lactococcus lactis. Journal of Bacteriology.* 1994, vol. 176, no. 21, p. 6457-63.

KIM, et al. Complete sequence of the UPP gene encoding uracil phosphoribosyltransferase from *Mycobacterium bovis* BCG. *Biochemistry and molecular biology international.* 1997, vol. 41, no. 6, p. 1117-24.

MARTINUSSEN, et al. Two genes encoding uracil phosphoribosyltransferase are present in *Bacillus subtilis. Journal of Bacteriology.* 1995, vol. 177, no. 1, p. 271-4.

KERN, et al. The FUR1 gene of *Saccharomyces cerevisiae*: cloning, structure and expression of wild-type and mutant alleles. *Gene.* 1990, vol. 88, no. 2, p. 149-57.

CHAKRABARTI. *Biotechniques.* 1997, no. 23, p. 1094-97.

HAMMOND, et al. *Journal of Virological Methods.* 1997, no. 66, p. 135-38.

KUMAR. *Virology.* 1990, no. 179, p. 151-8.

The invention claimed is:

1. A method for treating a disease state, wherein a defective poxvirus whose genome is only defective of the F2L and JR2 genes is administered to a host organism or cell which is in need of such treatment.

2. The method as defined by claim 1, wherein said poxvirus is administered via the systemic route.

3. The method as defined by claim 1, further comprising an additional step in which pharmaceutically acceptable quantities of a prodrug are administered to said host organism or cell.

4. The method as defined by claim 3, wherein the administration of said prodrug takes place at least 3 days after the administration of said poxvirus.

5. The method as defined by claim 4, wherein the administration of said prodrug takes place 7 days after the administration of said poxvirus.

6. A method for the treatment of cancer, comprising administering to a host organism or cell in need of such treatment, for such period of time as required to elicit the desired effect, a thus effective amount of a poxvirus whose genome is only defective of the F2L and J2R genes.

* * * * *

SEQUENCE LISTING

```
<160> NUMBER OF SEQ ID NOS: 12

<210> SEQ ID NO 1
<211> LENGTH: 373
<212> TYPE: PRT
<213> ORGANISM: Saccharomyces cerevisiae

<400> SEQUENCE: 1

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
```

```
                    85                  90                  95
Ala Ile Ile Met Tyr Gly Ile Pro Arg Cys Val Val Gly Glu Asn Val
                100                 105                 110

Asn Phe Lys Ser Lys Gly Glu Lys Tyr Leu Gln Thr Arg Gly His Glu
            115                 120                 125

Val Val Val Asp Asp Glu Arg Cys Lys Lys Ile Met Lys Gln Phe
        130                 135                 140

Ile Asp Glu Arg Pro Gln Asp Trp Phe Glu Asp Ile Gly Glu Ala Ser
145                 150                 155                 160

Glu Pro Phe Lys Asn Val Tyr Leu Leu Pro Gln Thr Asn Gln Leu Leu
                165                 170                 175

Gly Leu Tyr Thr Ile Ile Arg Asn Lys Asn Thr Thr Arg Pro Asp Phe
                180                 185                 190

Ile Phe Tyr Ser Asp Arg Ile Ile Arg Leu Leu Val Glu Glu Gly Leu
                195                 200                 205

Asn His Leu Pro Val Gln Lys Gln Ile Val Glu Thr Asp Thr Asn Glu
        210                 215                 220

Asn Phe Glu Gly Val Ser Phe Met Gly Lys Ile Cys Gly Val Ser Ile
225                 230                 235                 240

Val Arg Ala Gly Glu Ser Met Glu Gln Gly Leu Arg Asp Cys Cys Arg
                245                 250                 255

Ser Val Arg Ile Gly Lys Ile Leu Ile Gln Arg Asp Glu Glu Thr Ala
                260                 265                 270

Leu Pro Lys Leu Phe Tyr Glu Lys Leu Pro Glu Asp Ile Ser Glu Arg
            275                 280                 285

Tyr Val Phe Leu Leu Asp Pro Met Leu Ala Thr Gly Gly Ser Ala Ile
        290                 295                 300

Met Ala Thr Glu Val Leu Ile Lys Arg Gly Val Lys Pro Glu Arg Ile
305                 310                 315                 320

Tyr Phe Leu Asn Leu Ile Cys Ser Lys Glu Gly Ile Glu Lys Tyr His
                325                 330                 335

Ala Ala Phe Pro Glu Val Arg Ile Val Thr Gly Ala Leu Asp Arg Gly
            340                 345                 350

Leu Asp Glu Asn Lys Tyr Leu Val Pro Gly Leu Gly Asp Phe Gly Asp
        355                 360                 365

Arg Tyr Tyr Cys Val
        370

<210> SEQ ID NO 2
<211> LENGTH: 373
<212> TYPE: PRT
<213> ORGANISM: Artificial
<220> FEATURE:
<223> OTHER INFORMATION: derived from Saccharomyces cerevisiae

<400> SEQUENCE: 2

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
                20                  25                  30

Ile Gly Gly Cys Leu Ile Asn Asn Lys Asp Gly Ser Val Leu Gly Arg
            35                  40                  45

Gly His Asn Met Arg Phe Gln Lys Gly Ser Ala Thr Leu His Gly Glu
        50                  55                  60

Ile Ser Thr Leu Glu Asn Cys Gly Arg Leu Glu Gly Lys Val Tyr Lys
```

```
                 65                  70                  75                  80
Asp Thr Thr Leu Tyr Thr Thr Leu Ser Pro Cys Asp Met Cys Thr Gly
                 85                  90                  95
Ala Ile Ile Met Tyr Gly Ile Pro Arg Cys Val Val Gly Glu Asn Val
                100                 105                 110
Asn Phe Lys Ser Lys Gly Glu Lys Tyr Leu Gln Thr Arg Gly His Glu
                115                 120                 125
Val Val Val Asp Asp Glu Arg Cys Lys Lys Ile Met Lys Gln Phe
                130                 135                 140
Ile Asp Glu Arg Pro Gln Asp Trp Phe Glu Asp Ile Gly Glu Ala Ser
145                 150                 155                 160
Glu Pro Phe Lys Asn Val Tyr Leu Leu Pro Gln Thr Asn Gln Leu Leu
                165                 170                 175
Gly Leu Tyr Thr Ile Ile Ser Asn Lys Asn Thr Thr Arg Pro Asp Phe
                180                 185                 190
Ile Phe Tyr Ser Asp Arg Ile Ile Arg Leu Leu Val Glu Gly Leu
                195                 200                 205
Asn His Leu Pro Val Gln Lys Gln Ile Val Glu Thr Asp Thr Asn Glu
                210                 215                 220
Asn Phe Glu Gly Val Ser Phe Met Gly Lys Ile Cys Gly Val Ser Ile
225                 230                 235                 240
Val Arg Ala Gly Glu Ser Met Glu Gln Gly Leu Arg Asp Cys Cys Arg
                245                 250                 255
Ser Val Arg Ile Gly Lys Ile Leu Ile Gln Arg Asp Glu Thr Ala
                260                 265                 270
Leu Pro Lys Leu Phe Tyr Glu Lys Leu Pro Glu Asp Ile Ser Glu Arg
                275                 280                 285
Tyr Val Phe Leu Leu Asp Pro Met Leu Ala Thr Gly Gly Ser Ala Ile
                290                 295                 300
Met Ala Thr Glu Val Leu Ile Lys Arg Gly Val Lys Pro Glu Arg Ile
305                 310                 315                 320
Tyr Phe Leu Asn Leu Ile Cys Ser Lys Glu Gly Ile Glu Lys Tyr His
                325                 330                 335
Ala Ala Phe Pro Glu Val Arg Ile Val Thr Gly Ala Leu Asp Arg Gly
                340                 345                 350
Leu Asp Glu Asn Lys Tyr Leu Val Pro Gly Leu Gly Asp Phe Gly Asp
                355                 360                 365
Arg Tyr Tyr Cys Val
                370

<210> SEQ ID NO 3
<211> LENGTH: 644
<212> TYPE: PRT
<213> ORGANISM: Artificial
<220> FEATURE:
<223> OTHER INFORMATION: derived from Saccharomyces cerevisiae

<400> SEQUENCE: 3

Met Val Ser Asn Asn Ala Leu Glu Thr Ile Ile Asn Ala Arg Leu Pro
1               5                  10                  15
Gly Glu Glu Gly Leu Trp Gln Ile His Leu Gln Asp Gly Lys Ile Ser
                20                  25                  30
Ala Ile Asp Ala Gln Ser Gly Val Met Pro Ile Thr Glu Asn Ser Leu
                35                  40                  45
Asp Ala Glu Gln Gly Leu Val Ile Pro Pro Phe Val Glu Pro His Ile
```

```
            50                  55                  60
His Leu Asp Thr Thr Gln Thr Ala Gly Gln Pro Asn Trp Asn Gln Ser
 65                  70                  75                  80

Gly Thr Leu Phe Glu Gly Ile Glu Arg Trp Ala Glu Arg Lys Ala Leu
                 85                  90                  95

Leu Thr His Asp Asp Val Lys Gln Arg Ala Trp Gln Thr Leu Lys Trp
            100                 105                 110

Gln Ile Ala Asn Gly Ile Gln His Val Arg Thr His Val Asp Val Ser
            115                 120                 125

Asp Ala Thr Leu Thr Ala Leu Lys Ala Met Leu Glu Val Lys Gln Glu
            130                 135                 140

Val Ala Pro Trp Ile Asp Leu Gln Ile Val Ala Phe Pro Gln Glu Gly
145                 150                 155                 160

Ile Leu Ser Tyr Pro Asn Gly Glu Ala Leu Leu Glu Glu Ala Leu Arg
                165                 170                 175

Leu Gly Ala Asp Val Val Gly Ala Ile Pro His Phe Glu Phe Thr Arg
            180                 185                 190

Glu Tyr Gly Val Glu Ser Leu His Lys Thr Phe Ala Leu Ala Gln Lys
            195                 200                 205

Tyr Asp Arg Leu Ile Asp Val His Cys Asp Glu Ile Asp Asp Glu Gln
210                 215                 220

Ser Arg Phe Val Glu Thr Val Ala Ala Leu Ala His His Glu Gly Met
225                 230                 235                 240

Gly Ala Arg Val Thr Ala Ser His Thr Thr Ala Met His Ser Tyr Asn
                245                 250                 255

Gly Ala Tyr Thr Ser Arg Leu Phe Arg Leu Leu Lys Met Ser Gly Ile
            260                 265                 270

Asn Phe Val Ala Asn Pro Leu Val Asn Ile His Leu Gln Gly Arg Phe
            275                 280                 285

Asp Thr Tyr Pro Lys Arg Arg Gly Ile Thr Arg Val Lys Glu Met Leu
            290                 295                 300

Glu Ser Gly Ile Asn Val Cys Phe Gly His Asp Asp Val Phe Asp Pro
305                 310                 315                 320

Trp Tyr Pro Leu Gly Thr Ala Asn Met Leu Gln Val Leu His Met Gly
                325                 330                 335

Leu His Val Cys Gln Leu Met Gly Tyr Gly Gln Ile Asn Asp Gly Leu
            340                 345                 350

Asn Leu Ile Thr His His Ser Ala Arg Thr Leu Asn Leu Gln Asp Tyr
            355                 360                 365

Gly Ile Ala Ala Gly Asn Ser Ala Asn Leu Ile Ile Leu Pro Ala Glu
            370                 375                 380

Asn Gly Phe Asp Ala Leu Arg Arg Gln Val Pro Val Arg Tyr Ser Val
385                 390                 395                 400

Arg Gly Gly Lys Val Ile Ala Ser Thr Gln Pro Ala Gln Thr Thr Val
                405                 410                 415

Tyr Leu Glu Gln Pro Glu Ala Ile Asp Tyr Lys Arg Ile Ser Gly Ala
            420                 425                 430

Asn Gly Val Met Ala Lys Ile Val Glu Val Lys His Pro Leu Val Lys
            435                 440                 445

His Lys Leu Gly Leu Met Arg Glu Gln Asp Ile Ser Thr Lys Arg Phe
            450                 455                 460

Arg Glu Leu Ala Ser Glu Val Gly Ser Leu Leu Thr Tyr Glu Ala Thr
465                 470                 475                 480
```

```
Ala Asp Leu Glu Thr Glu Lys Val Thr Ile Glu Gly Trp Asn Gly Pro
            485                 490                 495

Val Glu Ile Asp Gln Ile Lys Gly Lys Lys Ile Thr Val Val Pro Ile
            500                 505                 510

Leu Arg Ala Gly Leu Gly Met Met Asp Gly Val Leu Glu Asn Val Pro
            515                 520                 525

Ser Ala Arg Ile Ser Val Val Gly Met Tyr Arg Asn Glu Glu Thr Leu
        530                 535                 540

Glu Pro Val Pro Tyr Phe Gln Lys Leu Val Ser Asn Ile Asp Glu Arg
545                 550                 555                 560

Met Ala Leu Ile Val Asp Pro Met Leu Ala Thr Gly Gly Ser Val Ile
            565                 570                 575

Ala Thr Ile Asp Leu Leu Lys Lys Ala Gly Cys Ser Ser Ile Lys Val
            580                 585                 590

Leu Val Leu Val Ala Ala Pro Glu Gly Ile Ala Ala Leu Glu Lys Ala
            595                 600                 605

His Pro Asp Val Glu Leu Tyr Thr Ala Ser Ile Asp Gln Gly Leu Asn
            610                 615                 620

Glu His Gly Tyr Ile Ile Pro Gly Leu Gly Asp Ala Gly Asp Lys Ile
625                 630                 635                 640

Phe Gly Thr Lys

<210> SEQ ID NO 4
<211> LENGTH: 158
<212> TYPE: PRT
<213> ORGANISM: Saccharomyces cerevisiae

<400> SEQUENCE: 4

Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155

<210> SEQ ID NO 5
<211> LENGTH: 150
<212> TYPE: PRT
<213> ORGANISM: Candida albicans

<400> SEQUENCE: 5
```

```
Met Ala Phe Asp Asp Lys Lys Gly Leu Gln Val Ala Leu Asp Gln Ala
1               5                   10                  15

Lys Lys Ser Tyr Ser Glu Gly Gly Ile Pro Ile Gly Ser Cys Ile Ile
            20                  25                  30

Ser Ser Asp Asp Thr Val Leu Gly Gln Gly His Asn Glu Arg Ile Gln
        35                  40                  45

Lys His Ser Ala Ile Leu His Gly Glu Met Ser Ala Leu Glu Asn Ala
    50                  55                  60

Gly Arg Leu Pro Gly Lys Thr Tyr Lys Asp Cys Thr Ile Tyr Thr Thr
65                  70                  75                  80

Leu Ser Pro Cys Ser Met Cys Thr Gly Ala Ile Leu Leu Tyr Gly Phe
                85                  90                  95

Lys Arg Val Val Met Gly Glu Asn Val Asn Phe Leu Gly Asn Glu Lys
                100                 105                 110

Leu Leu Ile Glu Asn Gly Val Glu Val Val Asn Leu Asn Asp Gln Glu
            115                 120                 125

Cys Ile Asp Leu Met Ala Lys Phe Ile Lys Glu Lys Pro Gln Asp Trp
130                 135                 140

Asn Glu Asp Ile Gly Glu
145             150

<210> SEQ ID NO 6
<211> LENGTH: 432
<212> TYPE: PRT
<213> ORGANISM: Escherichia coli

<400> SEQUENCE: 6

Met Trp Arg Leu Thr Val Ser Asn Asn Ala Leu Gln Thr Ile Ile Asn
1               5                   10                  15

Ala Gln Leu Pro Gly Lys Glu Gly Leu Trp Gln Ile His Leu His Asp
            20                  25                  30

Gly Lys Ile Ser Ala Ile Asp Ala Gln Ser Gly Val Met Pro Val Thr
        35                  40                  45

Glu Asn Ser Leu Asp Ala Glu Gln Gly Leu Val Leu Pro Pro Phe Val
    50                  55                  60

Glu Pro His Ile His Leu Asp Thr Thr Gln Thr Ala Gly Gln Pro Asn
65                  70                  75                  80

Trp Asn Gln Ser Gly Thr Leu Phe Glu Gly Ile Glu Arg Trp Ala Glu
                85                  90                  95

Arg Lys Ala Leu Leu Thr His Asp Asp Val Lys Gln Arg Ala Trp Gln
                100                 105                 110

Thr Leu Lys Trp Gln Ile Ala Asn Gly Ile Gln His Val Arg Thr His
            115                 120                 125

Val Asp Val Ser Asp Ala Thr Leu Thr Ala Leu Lys Ala Met Leu Glu
130                 135                 140

Val Lys Gln Glu Val Ala Pro Trp Ile Asp Leu Gln Ile Val Ala Phe
145                 150                 155                 160

Pro Gln Glu Gly Ile Leu Ser Tyr Pro Asn Gly Glu Ala Leu Leu Glu
                165                 170                 175

Glu Ala Leu Arg Leu Gly Ala Asp Val Val Gly Ala Ile Pro His Phe
            180                 185                 190

Glu Phe Thr Arg Glu Tyr Gly Val Glu Ser Leu His Lys Thr Phe Ala
        195                 200                 205

Leu Ala Gln Lys Tyr Asp Arg Leu Ile Asp Val His Cys Asp Glu Ile
    210                 215                 220
```

Asp Asp Glu Gln Ser Arg Phe Val Glu Thr Val Ala Ala Leu Ala His
225                 230                 235                 240

Arg Glu Gly Met Gly Ala Arg Val Thr Ala Ser His Thr Ala Met
            245                 250                 255

His Ser Tyr Asn Gly Ala Tyr Thr Ser Arg Leu Phe Arg Leu Leu Lys
        260                 265                 270

Met Ser Gly Ile Asn Phe Val Ala Asn Pro Leu Val Asn Ile His Leu
            275                 280                 285

Gln Gly Arg Phe Asp Thr Tyr Pro Lys Arg Arg Gly Ile Thr Arg Val
        290                 295                 300

Lys Glu Met Leu Glu Ser Gly Ile Asn Val Cys Phe Gly His Asp Asp
305                 310                 315                 320

Val Phe Asp Pro Trp Tyr Pro Leu Gly Thr Ala Asn Met Leu Gln Val
            325                 330                 335

Leu His Met Gly Leu His Val Cys Gln Leu Met Gly Tyr Gly Gln Ile
            340                 345                 350

Asn Asp Gly Leu Asn Leu Ile Thr His His Ser Ala Arg Thr Leu Asn
        355                 360                 365

Leu Gln Asp Tyr Gly Ile Ala Ala Gly Asn Ser Ala Asn Leu Ile Ile
        370                 375                 380

Leu Pro Ala Glu Asn Gly Phe Asp Ala Leu Arg Arg Gln Val Pro Val
385                 390                 395                 400

Arg Tyr Ser Val Arg Gly Gly Lys Val Ile Ala Ser Thr Gln Pro Ala
            405                 410                 415

Gln Thr Thr Val Tyr Leu Glu Gln Pro Glu Ala Ile Asp Tyr Lys Arg
            420                 425                 430

<210> SEQ ID NO 7
<211> LENGTH: 31
<212> TYPE: DNA
<213> ORGANISM: Artificial
<220> FEATURE:
<223> OTHER INFORMATION: Oligonucleotides

<400> SEQUENCE: 7
cgcggatccg aaagcgatga actaaatgtt c                           31

<210> SEQ ID NO 8
<211> LENGTH: 33
<212> TYPE: DNA
<213> ORGANISM: Artificial
<220> FEATURE:
<223> OTHER INFORMATION: Oligonucleotides

<400> SEQUENCE: 8
tcccccgggg ttagtttcct taacaaatct aac                         33

<210> SEQ ID NO 9
<211> LENGTH: 31
<212> TYPE: DNA
<213> ORGANISM: Artificial
<220> FEATURE:
<223> OTHER INFORMATION: oligonucleotides

<400> SEQUENCE: 9
gcctggccaa caaatagagg agatcaaggg t                           31

<210> SEQ ID NO 10
<211> LENGTH: 33

-continued

```
<212> TYPE: DNA
<213> ORGANISM: Artificial
<220> FEATURE:
<223> OTHER INFORMATION: oligonucleotides

<400> SEQUENCE: 10
gcccagctga ccactacatc aattttacaa aag                              33

<210> SEQ ID NO 11
<211> LENGTH: 32
<212> TYPE: DNA
<213> ORGANISM: Artificial
<220> FEATURE:
<223> OTHER INFORMATION: oligonucleotides

<400> SEQUENCE: 11
gccgcatgct ccagaattga tcatagtgga ta                               32

<210> SEQ ID NO 12
<211> LENGTH: 32
<212> TYPE: DNA
<213> ORGANISM: Artificial
<220> FEATURE:
<223> OTHER INFORMATION: oligonucleotides

<400> SEQUENCE: 12
gctctagagt tagtttcctt aacaaatcta ac                               32
```